United States Patent

Stupczewski et al.

[11] Patent Number: 6,004,982
[45] Date of Patent: Dec. 21, 1999

[54] 4-PIPERIDINYL) H-2-BENZOPYRAN DERIVATIVES USEFUL AS ANTIPSYCHOTIC AGENTS

[75] Inventors: Joseph T. Stupczewski, Flemington, N.J.; Kenneth J. Bordeau, Kintnersville; Shelley L. Pavlek, Langhorne, both of Pa.

[73] Assignee: Hoechst Marion Roussel, Inc., Bridgewater, N.J.

[21] Appl. No.: 09/010,720

[22] Filed: Jan. 22, 1998

Related U.S. Application Data

[60] Provisional application No. 60/084,196, Feb. 7, 1997.
[51] Int. Cl.$^6$ ........................ A61K 31/445; C07D 405/04
[52] U.S. Cl. ............................................. 514/320; 546/196
[58] Field of Search ............................ 846/196; 514/370

[56] References Cited

U.S. PATENT DOCUMENTS

| | | | |
|---|---|---|---|
| 3,824,244 | 7/1974 | Houlihan et al. | 546/283.1 |
| 4,153,612 | 5/1979 | McCall | 549/355 |
| 4,487,774 | 12/1984 | MCall | 514/322 |
| 4,577,021 | 3/1986 | MCall | 544/376 |
| 4,963,568 | 10/1990 | Schoenleber et al. | 514/320 |
| 4,994,486 | 2/1991 | Schoenleber et al. | 514/456 |
| 5,532,241 | 7/1996 | Bottcher et al. | 514/254 |
| 5,545,643 | 8/1996 | Heine et al. | 514/322 |
| 5,591,884 | 1/1997 | DiNinno et al. | 558/286 |

FOREIGN PATENT DOCUMENTS 1552004  9/1979  United Kingdom.

OTHER PUBLICATIONS

Schoenleber et al. "Preparation of 1–aminomethyl–5,6–dihydroxy–3,4–dihydro–1H–2–benzopyrans . . . " CA 126:104008, 1996.
Burger "A guide to the chemical basis of drug design" Wiley Interscience, p. 15, 1983.
M. R. Michaelides, et al., J. Med. Chem. 34, pp. 2946–2953 (1991).
M.P. DeNinno, et al., J. Med. Chem, pp. 2561–2569 (1991).
D. Davidson, et al., Arch. Gen,. Psychiatry 47 pp. 190–191 (1990).
M. DeNinno et al., J. Med. Chem. 33, pp. 2948–2950 (1990).
M.DeNinno et al., J. Org. Chem. 57 pp. 7115–7118 (1992).
C. Sanchez, et al., Drug Dev. Res. 22, pp. 239–250 (1991).
U. Schollkopf et al., Liebigs Ann. Chem pp. 969–977 (1976) (German language).

*Primary Examiner*—Ceila Chang
*Attorney, Agent, or Firm*—Carolyn D. Moon

[57] ABSTRACT

The present invention comprises (4-Piperidinyl)-1H-2-Benzopyran derivatives useful as antipsychotic agents, their intermediates, pharmaceutical compositions and methods of making these compounds. These compounds are useful in treating psychosis.

75 Claims, No Drawings

4-PIPERIDINYL) H-2-BENZOPYRAN DERIVATIVES USEFUL AS ANTIPSYCHOTIC AGENTS

This application claims the benefit of Provisional Application No. 60/084,196, filed Sep. 15, 1997.

FIELD OF THE INVENTION

The present invention is related to intermediates for making novel compounds, novel compounds, a method of treating psychosis by administering the novel compounds, and a method of making these compounds.

BACKGROUND OF THE INVENTION

Psychosis is a disorder which grossly interferes with the capacity to meet ordinary demands of life. Conceptually, it is a loss of ego boundaries or a gross impairment in reality testing. Included under the term pyschosis are the disorders Schizophrenia, Schizophreniform Disorder, Schizoaffective Disorder, Delusional Disorder, Brief Psychotic Disorder, Shared Psychotic Disorder, Psychotic Disorder due to a General Medical Condition, Substance-Induced Psychotic Disorder and Psychotic Disorder Not Otherwise Specified, as defined by the DIAGNOSTIC AND STATISTICAL MANUAL OF MENTAL DISORDERS, FOURTH EDITION, published 1994 by the American Psychiatric Association, Washington D.C. USA, incorporated herein by reference.

Schizophrenia is a disorder of thought which is characterized by positive (delusions, hallucinations, markedly bizarre behavior) and negative (flat affect, poverty of speech, social isolation, anhendonia) symptoms. The development of schizophrenia is thought to be due to an excess of dopaminergic transmission in the brain. This theory has been proposed based on the observations that typical antipsychotic drugs block $D_2$-type dopamine receptors, and drugs which increase the level of dopamine cause a psychosis that resembles the paranoid subtype of schizophrenia. Losoncyzy, M. F., et al., "The Dopamine Hypothesis of Schizophrenia", H. Y. Meltzer, ed., *Psychopharmacology: The Third Generation of Progress*. New York: Raven Press; 1987: 715–726.

There are presently therapeutic treatments available for treating psychosis by administering to the patient neuroleptic drugs such as chlorpromazine, haloperidol, and sulpride, for example. Of course, many of these drugs have unwanted side effects (e.g. extrapyramidal symptoms) or are not as effective as desired by all patients. Therefore, the need for different drug therapies still exists.

SUMMARY OF THE INVENTION

The present invention is a compound of Formula I

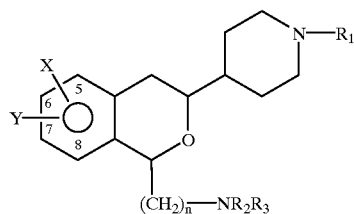

Formula I a stereoisomer, or a pharmaceutically acceptable salt thereof, wherein $R_1$ is H, $C_{1-6}$ alkyl, optionally substituted aralkyl, optionally substituted heteroarylalkyl, 5,5-dimethyl-1,1-dioxo-4-thiazolidinone, indan, $C_{1-6}$ alkylsulfonyl, trifluoroacetyl, or $(CH_2)_m Z(CH_2)_t$ optionally substituted phenyl, wherein Z is O or C=O;

wherein optionally substituted means a moiety is suitably substituted with one, two or three substituents each independently selected from H, halogen, $C_{1-6}$ alkyl, $C_{1-6}$ alkoxy, C(=O)H, C(=O)$C_{1-6}$ alkyl, $CF_3$ or hydroxy;

each of $R_2$ and $R_3$ are independently H, $C_{1-6}$ alkyl, —C(O)$C_{1-6}$alkyl, CHO, or $C_{2-6}$ alkenyl;

each of X and Y are independently H, hydroxy, $C_{1-6}$ alkyl, halogen, acyloxy or $C_{1-6}$ alkoxy, benzyloxy, or X and Y together form a diphenylmethylene ketal, cyclohexylidene ketal, methylene acetal or cyclic carbonate group provided that X and Y are adjacently positioned; and n is an integer 1, 2 or 3;

m is an integer 0, 1, 2 or 3; and t is an integer 0, 1, 2 or 3.

The present invention also comprises a pharmaceutical composition comprising the compound of formula I and a pharmaceutically acceptable carrier; a method of treating a patient for a psychotic disorder, in particular schizophrenia, by administering to the patient a therapeutically effective amount of the compound of formula I; and a method of making the compound of formula I.

An object of the present invention is to provide a novel compound useful in treating a psychotic disorder. Another object of the present invention is the use of this compound for treating a medical disorder, in particular pychosis and especially schizophrenia.

DESCRIPTION OF THE PRESENT INVENTION

Certain terms as used herein will have specified definitions:

(1) "Aralkyl" means an aryl or diaryl moiety connected to the remainder of the molecule via an alkylene bridge. This alkylene bridge can be straight or branched-chained and is one, two, three, four, five or six carbons in length. "Aryl" means an aromatic radical having six atoms in a single ring system such as phenyl or a fused ring system such as 1-naphthyl, 2-naphthyl and the like. The aryl or diaryl group may be optionally substituted as described herein. The substitutions may be at the ortho, meta or para positions as appropriate. Examples of preferred aralkyls are benzyl, phenylethyl, propylphenyl, and diphenylbutyl.

(2) "Optionally substituted" means that the referenced moiety is substituted as defined herein by same or different substituents, i.e. independently selected, from the group of hydrogen, halogen (fluorine, chlorine, iodine or bromine), $C_{1-6}$alkyl, $C_{1-6}$alkoxy, C(=O)H, C(=O)$C_{1-6}$alkyl, $CF_3$ or hydroxy with one, two or three substitutents as is suitable to the structure.

(3) "Heteroaralkyl" means a heteroaryl connected to the rest of the molecule by an alkylene bridge. This alkylene bridge can be straight or branched-chained and is one, two, three, four, five or six carbons in length. The "Heteroaryl" portion refers to an aromatic moiety of five or six members with one, two or three members thereof being an oxygen, nitrogen, sulfur or combinations thereof. Some examples of five-membered heteroaryls are thiophene, furan, pyrrole, imidazole, pyrazole, isothiazole, and isoxazole. Some examples of six-membered heteroaryls are pyran, pyridine, pyrazine, pyrimidine, and pyridazine. Heteroaryls may also be a fused ring aromatic system having one, two or three members thereof being an oxygen, nitrogen, sulfur or combinations thereof such as benzothiophene, chromene, indolizine, isoindole, indole, indazole, quinoline, 2-oxo-2,3-dihydrobenzimidazyl, phthalazine, quinazoline, cinnoline, isochroman, chroman, 1,2-benzenedicarboximide and benzisoxazole. The heteroarylalkyl may be optionally substituted at the heteroaryl portion thereof as described herein.

(4) "Patient" means a mammal such as a dog, cat, guinea pig, mouse, rat or human being.

(5) "Treating" or "to treat" means to alleviate symptoms, eliminate the causation either on a temporary or permanent basis, or to prevent or slow the appearance of symptoms of the named disorder.

(6) "Psychotic Disorder" or "psychosis" are used interchangably and have the meaning defined in this specification.

(7) "$C_{1-6}$ alkyl", used alone or in combination with other terms means an alkyl (or alkylene as appropriate), straight or branched-chain, which has one, two, three, four, five or six carbons or ranges thereof, e.g. $C_{1-2}$, $C_{1-3}$, $C_{1-4}$, $C_{2-3}$, $C_{2-4}$, etc. Some examples are methyl, ethyl, propyl, butyl, isopropyl, isobutyl, t-butyl, n-pentyl, 1-methylbutyl, 2,2-dimethylbutyl and the like. Likewise "$C_{1-6}$ alkoxy" may have one, two, three, four, five or six straight or branched-chain carbons or ranges thereof such as methoxy, ethoxy, etc.

(8) "Stereoisomer" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereoisomers).

(9) "Pharmaceutically acceptable salt" means either an acid addition salt or a basic addition salt which is compatible with treatment of patients for the intended use.

"Pharmaceutically acceptable acid addition salt" is a non-toxic organic or inorganic acid addition salt of the base compounds represented by Formula (I) or any of its intermediates. Some examples of inorganic acids which form suitable salts include hydrochloric, hydrobromic, sulphuric, and phosphoric acid and acid metal salts such as sodium monohydrogen orthophosphate, and postassium hydrogen sulfate. Illustrative organic acids which form suitable salts include the mono-, di-, and tricarboxylic acids. Examples of such acids are acetic, glycolic, lactic, pyruvic, malonic, succinic, glutaric, fumaric, malic, tartaric, citric, ascorbic, maleic, hyrdroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hyroxyethane sulfonic acid. Such salts can exist in either a hydrated or substantially anhydrous form. In general, the acid addition hydrophilic organic salts in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium, or barium hydroxides; ammonia, and aliphatic, alicyclic, or aromatic organic amines such as methylamine, trimethylamine, and picoline.

(10) "Therapeutically effective amount" means an amount of the compound which is effective in treating the named disorder.

The variables X and Y of Formula I, when adjacently positioned can form a diphenylmethylene ketal, methylene acetal, cyclohexylidene ketal, or cyclic carbonate group which are respectively shown hereafter:

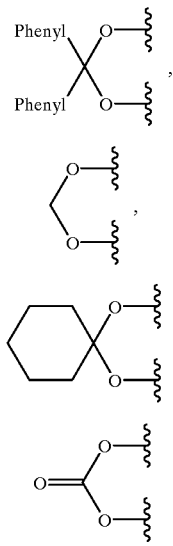

These groups, not including the oxygens, are sometimes considered "catechol protecting groups". Their synthesis is described in Protective Groups in Organic Synthesis, second edition, by Greene, T., et al. published by John Wiley and Sons, Inc., both incorporated herein by reference and *J. Med. Chem.* 34:2561–2569 (1991). It is intended that the present invention cover these and other conventional protecting groups known to those skilled in the art.

The compounds of the invention may be prepared by the synthetic routes described below in the Schemes or other methods which may be apparent to those skilled in the art.

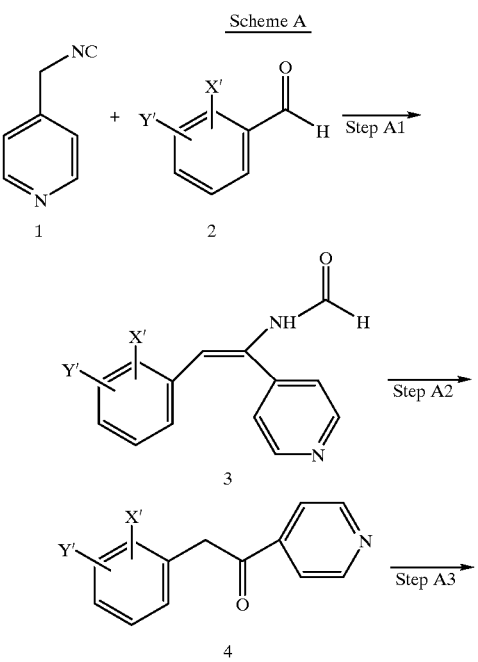

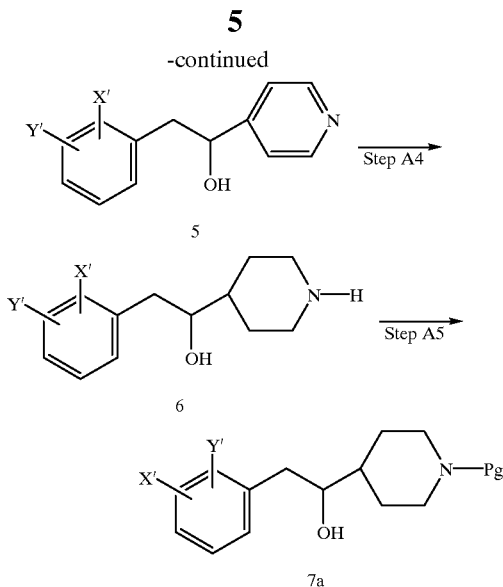

In Scheme A, Y' and X' represent Y and X as previously defined except for the hydroxy moiety, and are preferably $C_{1-6}$ alkoxy or together form cyclohexylideneketal, and more preferably are at the 5 and 6 positions of the benzopyran.

Step A1: The isocyanide 1 can be made from the commercially available (Aldrich) 4-(aminomethyl)pyridine which is reacted with ethyl formate to form 4-[(N-methyl)formamide]pyridine which is converted to an isocyanide 1. One method to accomplish the foregoing is by elimination of water with phosgene and a tertiary amine. For example, triphenylphosphine and triethylamine are reacted with 4-[(N-methyl)formadine]pyridine in the presence of carbon tetrachloride and dichloromethane to produce the isocyanide 1. The isocyanide 1 is condensed with the benzaldehyde 2 to provide the formamide 3 which is hydrolyzed in an acidic medium to the ethanone 4 (see V. Schöllkopf et al., *Liebig's Ann. Chem.* 1976: pp. 969–977). The condensation of the isocyanide 1 with the benzaldehyde 2 to a vinylformamide 3 may be accomplished with an alkaline metal alkoxide such as potassium t-butoxide to initiate the reaction in an ethereal solvent, preferably tetrahydrofuran. The reaction temperature may vary between 0° C. and the boiling point of the solvent. The preferred temperature is between 0° C. and room temperature.

Step A2: The vinylformamide 3 is converted to the 4-acylpyridine 4. The reaction may be carried out in a protic solvent such as methanol using a mineral acid, preferably concentrated hydrochloric acid. The reaction temperature may vary between 0° C. and the boiling point of the solvent, but 0° C. to 40° C. is preferred.

Step A3: The 4-acylpyridine 4 is reduced to alcohol 5 by use of any appropriate reducing agent such as lithium aluminum hydride, alkaline earth borohydrides and the like, sodium borohydride being the preferred reducing agent. The reaction preferably is carried out in an appropriate solvent such as ethanol at a temperature range from 0° C. to the boiling point of the solvent with room temperature, about 22° C., being preferred.

Step A4: The reduction of the pyridine ring of alcohol 5 to a piperidine ring to afford piperidine 6 is accomplished by hydrogenating alcohol 5 in the presence of a catalyst under acidic conditions. Examples of catalysts which may be used are those containing rhodium, palladium or platinum of which platinum oxide is preferred. Acidic reaction conditions may be obtained by conducting the reaction in an alkanoic acid as solvent. Examples of alkanoic acids which may be used are acetic, propionic or butyric acids. Acetic acid is preferred. Under these conditions, the hydrogenation proceeds at a reasonable rate under a hydrogen pressure within the range of about atmospheric pressure to 5 atmospheres of hydrogen pressure. A hydrogenation pressure of one atmosphere is preferred.

Step A5: The piperidine 6 is reacted with Lg-Pg wherein Lg is a suitable leaving group such as halogen and Pg is a protecting group such as $C_{1-6}$ alkylsulfonyl, trifluoroacetyl, or $C(=O)C_{1-6}$ alkyl. More preferably Pg is trifluroacetyl, methylsulfonyl or acetyl and Lg is chloride or anhydride which may be formed using standard acid chloride formation techniques.

Scheme B shows an alternative method for obtaining the intermediate 7b useful in producing compounds of the present invention.

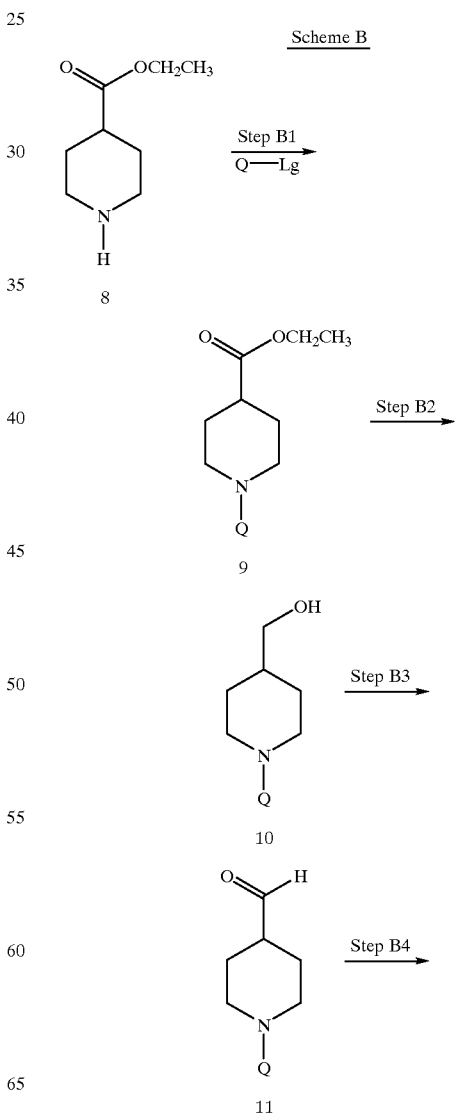

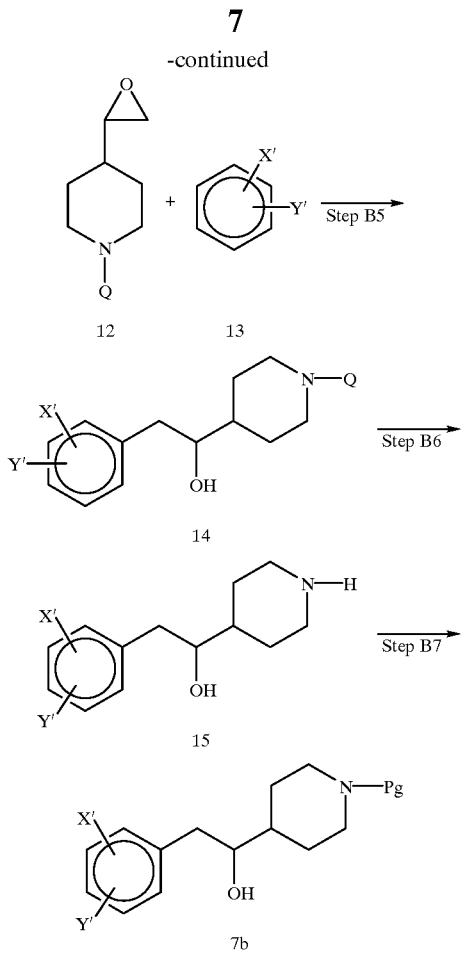

Step B1: Ethyl isonipecotate 8 is reacted with Lg-Q and ethanol, wherein Lg is a suitable leaving group such as a halogen and Q is a moiety, such as benzyl. The reaction takes place in the presence of an inorganic base such as potassium carbonate, preferably in the presence of a solvent such as an alcohol such as ethyl alcohol to produce the ester 9.

Step B2: The ester 9 is reduced with a suitable reducing agent such as lithium aluminum hydride in THF to produce the alcohol 10.

Step B3: An oxidation of the alcohol 10 provides the aldehyde 11. The Swern oxidation is preferred.

Step B4: Epoxidation of the aldehyde 11 preferably in the presence of a suitable solvent provides the epoxide 12. For example, the aldehyde 11 may be added to a solution $(CH_3)_3SOI/KOt$-Bu in DMSO and at about room temperature.

Step B5: The substituted phenyl 13 is reacted with the epoxide 12 to produce the intermediate 14. Different solvents and conditions may be employed when certain X', Y' and Q moieties are employed which will be known to those skilled in the art. For example, when X' and Y' form a cyclohexylidene ketal, a base such as nBuLi in THF may be used.

Step B6: The intermediate 14 is deprotected by removing the Q moiety to produce the piperidine 15. This may be accomplished by the use of a hydrogenation source, preferably in the presence of a suitable catalyst and solvent. For example, when Q is benzyl, cylclohexene and a palladium catalyst in the presence of methanol is reacted with piperidine 15. The mixture is heated to reflux for about 1–10 hours.

Step B7: The piperidine 15 is selectively protected next by adding the protecting group (Pg) at the nitrogen. Any appropriate protecting group may be used which prepares the piperidine 15 for the cyclization step. One method is to provide as the protecting group trifluoroacetyl, $C_{1-6}$ alkyl—C(O)—, or $C_{1-6}$ sulfonyl with trifluoroacetyl being preferred. Piperidine 15 may be reacted with an appropriate anhydride such as trifluoroacetic anhydride in a suitable solvent such as dichloromethane. An addition of an acid scavenger such as triethylamine may be useful to the reaction. The trifluoroacetyl is positioned on both the nitrogen and the oxygen of the former hydroxy group at this point. The hydroxy can be reformed by selective deprotection means, preferably by basic hydroylsis by an inorganic base such as potassium carbonate in a suitable solvent such as methanol. This produces the protected nitrogen-unprotected hydroxy intermediate 7b which is now ready for the cyclization step shown in Scheme C.

SCHEME C

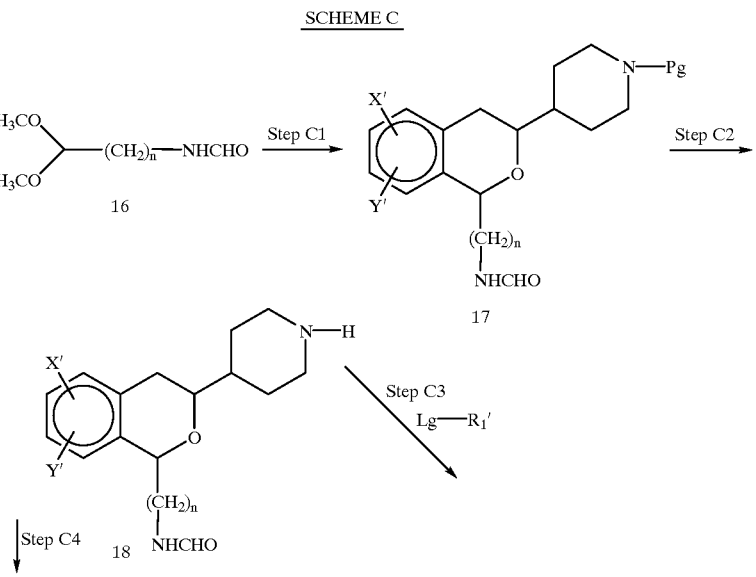

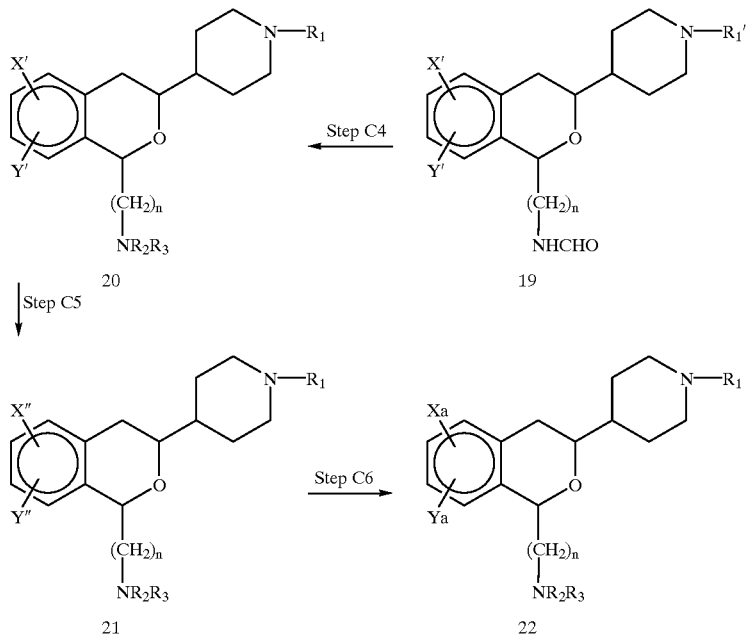

Step C1: The hydroxypiperidine 7 (which can be either 7a from Scheme A or 7b from Scheme B) is reacted with the amide 16 in a suitable nonprotic inert solvent to form the formamide 17. Examples of suitable nonprotic inert solvents are members of the halohydrocarbon group of solvents with dichloromethane being preferred. The reaction mixture is then treated with a suitable Lewis acid catalyst. Examples of suitable Lewis acid catalysts are trimethylsilyl triflate or boron trifluoride etherate with boron trifluoride etherate being preferred. The cyclization may be carried out at about 0 degrees C. to about room temperature. The preferred starting temperature is 0 degrees C., after which the reaction is allowed to warm to room temperature to provide the benzopyran 17. See M. P. DeNinno et al., *Journal of Medicinal Chemistry*, volume 34, pp. 256–2569 (1991), incorporated herein by reference.

The formamide 17 produced has a Pg moiety which represents Pg from Scheme A or Pg from Scheme B. X' and Y' represent X and Y when both X and Y are not hydroxy and are preferably a protected form of oxygen (acyloxy, $C_{1-6}$ alkoxy, benzyloxy or X and Y together form diphenylmethylene ketal, cyclohexylidene ketal, methylene acetal or cyclic carbonate group). Pg is preferably $C(O)CF_3$, $C(O)CH_3$ or $S(O)_2CH_3$.

The formamide 17 now represents some of the compounds of the present invention and serves as a basis to make other compounds of Formula I. In order to produce all variables of Formula I, certain additional optional steps can be performed which may be referred to as deprotection steps, many of which are exemplified herein. See also Protective Groups in Organic Synthesis, 2nd ed., Theodora W. Greene, et al. John Wiley and Sons, Inc., incorporated herein by reference. "Optional" or "optionally" means that these steps may be used to produce further compounds which fall within the scope of Formula I.

Step C2: If Pg is not the desired $R_1$ moiety, then Pg may be reduced to hydrogen by use of a suitable reducing agent such as sodium borohydride to produce the piperidine 18 or if Pg is the proper moiety desired at the $R_1$ position the remaining amine can be deprotected to the appropriate $R_2/R_3$ moiety (Step C4). Likewise, X' and Y' can be deprotected (Step C5).

Step C3: If hydrogen is desired as the $R_1$ position, further steps at $R_2/R_3$ and X/Y positions can occur. If hydrogen is not the desired $R_1$ position, compound 18 can be reacted with $LgR_1'$ to produce compound 19.

For example, when the substituent to be added at the $R_1$ position is an alkyl, optionally substituted aralkyl, an optionally substituted heteroaralkyl or $-(CH_2)_mC(=O)(CH_2)_t$- optionally substituted phenyl, the piperidine may be heated in an inert solvent with the substituent of choice having a leaving group (Lg) such as a halide in the presence of a base to neutralize the acid liberated by the reaction. A suitable catalytic amount of an alkaline earth iodide may be added to accelerate the rate of reaction when appropriate.

Among the inert solvents which may be employed are aromatic hydrocarbons such as benzene, toluene and the like, as well as more polar solvents such as acetonitrile and dimethylformamide. Preferred solvents are toluene or acetonitrile.

The base used in the reaction may be selected from the group of alkaline earth carbonates or bicarbonates, with potassium carbonate the preferred inorganic base. A preferred catalyst is potassium iodide in an amount of about 0.01 to about 0.10 mole equivalents of alkylating agent being used. The reaction may be carried out at a suitable temperature such as within the range of 22° C. to the boiling point of the solvent. When toluene is used as a solvent it is preferable to heat the mixture. The reaction is carried out at reflux, that is, at the boiling point of the solvent.

The substituent-leaving groups ($R_1'$-Lg) that may be used to introduce the corresponding $R_1'$ group at the piperidine nitrogen are well known in the art, commercially available or may be made by those skilled in the art. The halide leaving group is selected from the group of chlorine, bromine and iodine. $R_1'$ is used to indicate the group encompassed by $R_1$ but not including H.

Step C4: If the desired $R_2$ group is H and the desired $R_3$ group is CHO, other steps regarding the X and Y positions can occur now. If other groups at the $R_2$ and $R_3$ positions are desired, the following steps may occur. Compound 19 may optionally be deprotected by removing the formyl group which would provide either two hydrogens, or a hydrogen and a $C_{1-6}$ alkyl group. The compound should be alkylated before removal of the formyl. Subsequent mono- or di-alkylation at this point can provide R2/R3 comprising one or two $C_{1-6}$ alkyl groups.

For example, the nitrogen protecting group may be removed by acid hydrolysis, preferably by heating with hydrochloric acid in ethanol, preferably heating with 3.0 N hydrochloric acid at reflux. The amine produced by deprotection may be monoalkylated by introducing the alkyl-leaving group. This procedure may be repeated to obtain the dialkylated amine. Alternatively, a reducing agent such as LAH can be added from room temperature to reflux temperature of the solvent to provide a mono-alkylated amine.

Step C5: The oxygen protecting groups as part of X and Y (if present)represented by X' and Y' may be cleaved by methods well known in the art to provide X" and Y" as hydroxy. For example, when X' and/or Y' are $C_{1-6}$ alkoxy the compounds 18 or 19 are heated with 48% hydrobromic acid, by use of aluminum chloride, or cleavaged with boron tribromide. The alkoxy cleavage with boron tribromide may be carried out at lower temperatures, within the range of −78° C. to 0° C. in an inert solvent such as selected from the halohydrocarbons. The preferred temperature range is from −78° C. to −30° C., and in the presence of a solvent such as dichloromethane.

Step C6: If it is desired that X and Y are acyloxy (Xa and Ya), the hydroxy groups present may be acylated with R—C(=O)halogen or (RCO)$_2$O where R is a $C_{1-6}$ alkyl.

Various starting materials are commercially available or easily made by one skilled in the art. For example, commercially available starting materials for compound 2 comprise 2,5-dimethylbenzaldehyde (Aldrich), 5-bromo-2-ethoxybenzaldehyde (Lancaster), 2-fluoro-5-methoxybenzaldehyde (Lancaster), 2,5-dimethylbenzaldehyde (Aldrich), 2,5-difluorobenzaldehyde (Aldrich), and 5-bromo-2-fluorobenzaldehyde (Lancaster). The benzyloxybenzaldehyde can be made by reacting benzyl bromide or benzyl chloride with 2,5-dihydroxybenzaldehyde (Aldrich), 3,4-dihydroxybenzaldehyde (Aldrich), or 2,4-dihydroxybenzaldehyde (Aldrich). Other commmercially available starting materials represented by compound 2 comprise 3-fluoro-p-anisaldehyde (also known as 3-fluoro-4-methoxybenzaldehyde) (Aldrich), 3,4-dimethoxybenzaldehyde (Aldrich), 3-benzyloxy-4-methoxybenzaldehyde (Aldrich), 4-benzyloxy-3-methoxybenzaldehyde (Aldrich), 3-ethoxy-4-methoxybenzaldehyde (Aldrich), 3-bromo-4-methoxybenzaldehyde (Aldrich), 3-chloro-4-methoxybenzaldehyde (Aldrich), 3-4-diethoxybenzaldehyde (Pflatz & Bauer), 4-ethoxy-3-methoxybenzaldehyde (Lancaster), 3,4-dimethylbenzaldehyde (Lancaster), 3,4-dichlorobenzaldehyde (Aldrich), 3,4-difluorobenzaldehyde (Aldrich), 3-chloro-4-fluorobenzyl-aldehyde (Aldrich), 4-chloro-3-fluorobenzaldehyde (Lancaster), 4-benzyloxy-3-methoxybenzaldehyde (Aldrich), 3-benzyloxy-4-methoxybenzaldehyde (Aldrich), piperonal (Aldrich), diphenylmethyleneketalbenzaldehyde (Salor), 2,4-dimethoxybenzaldehyde (Aldrich), 2-fluoro-4-methoxybenzaldehyde (Fluorochem), 4-fluoro-2-methoxybenzaldehyde (Wychem), 2,4-dimethylbenzaldehyde (Aldrich), 2,4-dichlorobenzaldehyde (Aldrich), 2,4-difluorobenzaldehyde (Aldrich), 4-bromo-2-fluorobenzaldehyde (Lancaster).

For compound 16 wherein n=3, aminobutyraldehydedimethyl (Airproducts) can be reacted with formaldehyde; wherein n=2, 1,1-dimethoxy-3-nitropropane (E-Merck) can be reduced to the amine and reacted with formaldehyde or alternatively the method according to J. Med. Chem. (1991) vol. 34, no. 8, p. 2561–2569 can be used starting with (H$_3$CO)$_2$CH(CH$_2$)$_2$Br. For compound 16 wherein n=1, aminoacetaldehyde dimethylacetal (Aldrich) can be formylated, e.g., Chem. Pharm. Bull. 42(8), 1655–1657 (1994).

When X and Y form a cyclic carbonate, 2,3-(methylenedioxy)benzaldehyde (Aldrich) may be used as starting material.

The foregoing steps may be combined or altered in sequence by those skilled in the art where considered appropriate. The use of the term "protecting group" is not meant to convey that a moiety containing a protecting group has no intended therapeutic activity.

The methodologies reported in the article by M. P. DeNinno et al., J. Med. Chem., 34: pp. 2561–2569 (1991), incorporated herein by reference, may be used to prepare compounds with various X and Y groups, and R$_2$ and R$_3$ groups.

Some specific examples of compounds of the present invention that may be made by the foregoing process follow. It is to be understood that the compounds of the present invention are not to be limited to the following examples but that the examples merely illustrate various compounds that may be made within the scope of the claims. Likewise, the sequence of the steps used in the following examples may be altered.

Abbreviations used herein have the following meanings: THF means tetrahydrofuran, CH$_2$Cl$_2$ means methylenedichloride, TLC means thin layer chromatography, EtOAC means ethyl acetate, Et$_2$NH means diethyl amine, IR means infrared spectrum, NMR means nuclear magnetic resonance spectrum, CHCl$_3$ means chloroform, CDCL$_3$ means deuterochloroform, MS means mass spectrum, HCl means hydrochloric acid, EtOH means ethyl alcohol, NaBH$_4$ means sodium borohydride, NaOH means sodium hydroxide, mp means melting point, C. means Centigrade, MeOH means methyl alcohol, BF$_3$O(Et)$_2$ means boron trifluoride etherate, Na$_2$CO$_3$ means sodium carbonate, h means hour, BBr$_3$ means boron tribromide, and LAH means lithium aluminum hydride.

EXAMPLE 1A

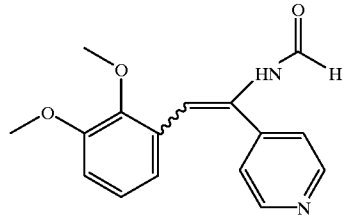

Intermediate: N-[2-(2,3-Dimethoxyphenyl)-1-(4-pyridinyl)vinyl]formamide

A solution of 4-(aminomethyl)pyridine (54.1 g, 0.5 mol) and ethyl formate (44.4 ml) was refluxed for two hours and then permitted to stand at ambient temperature for 16 hours. The reaction was distilled to produce 61.6 g of N-(4-pyridylmethyl)formamide.

A solution of N-(4-pyridylmethyl)formamide (27.7 g, 0.20 mol), carbon tetrachloride (26 g, 0.17 mol), triethylamine (16.8 g), triphenylphosphine (52.3 g, 0.2 mol) and dicholoromethane (170 ml) was refluxed for 3 hours. The reation was allowed to cool, it was filtered and the filtrate concentrated to a dark solid. The solid was triturated with 100 ml ether and allowed to stand at 25 degrees C. overnight. It was filtered again. The ether was evaporated to produce an oil mixture which was filtered to provide N-(4-pyridylmethyl)isocyanide.

To a stirred solution, under nitrogen, of potassium t-butoxide (39.9 g, 0.36 mol) in THF (400 ml), cooled to 0° C. was added, dropwise, N-(4-pyridylmethyl)isocyanide (20.8 g, 0.17 mol) dissolved in THF (100 ml), followed by the dropwise addition of 2,3-dimethoxybenzaldehyde (28.6 g, 0.17 mol) dissolved in THF (100 ml). The reaction was allowed to come to ambient temperature, and then HOAc (20.8 g) was added dropwise. The reaction was poured into water and the aqueous mixture was extracted with $CH_2Cl_2$. The extract was washed (brine), dried (magnesium sulfate) and concentrated to afford an off-white solid which was recrystallized twice from methanol to yield (1.2 g) of a white solid, mp 161–162° C.

Analysis: Calculated for $C_{16}H_{16}N_2O_3$: 67.59% C, 5.68% H, 9.85% N. Found: 67.50% C, 5.68% H, 9.73% N.

EXAMPLE 1B

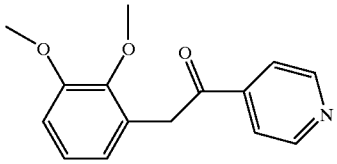

Intermediate: 2-(2,3-Dimethoxyphenyl)-1-(4-pyridinyl) ethanone

To a stirred suspension of N-[2-(2,3-dimethoxyphenyl)-1-(4-pyridinyl)vinyl]formamide (45.2 g, 0.16 mol) in methanol (400 ml), cooled to 0° C., was added, dropwise, concentrated HCl (120 ml). After complete addition, the temperature was raised to between 35–40° C. for 2 h. The reaction was allowed to stand at ambient temperature for 1 h, and after cooling it in an ice bath, 50% aqueous NaOH was added dropwise until the mixture was basic. Water was added and the resulting white precipitate was collected to yield the desired ketone which was removed and recrystallized twice from isopropanol to afford the titled compound as a white solid, mp 99–101° C.

Analysis: Calculated for $C_{15}H_{15}NO_3$: 70.02% C, 5.88% H, 5.44% N. Found: 69.86% C, 5.61% H, 5.32% N.

EXAMPLE 1C

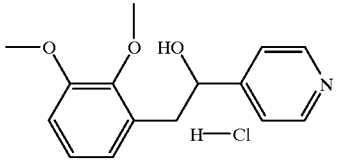

Intermediate: 4-[2-(2,3-Dimethoxyphenyl)-1-hydroxyethyl] pyridine Hydrochloride

To a stirred solution of 2-(2,3-dimethoxyphenyl)-1-(4-pyridinyl)ethanone (2.4 g, 0.009 mol) in EtOH (25 ml) was added, portionwise, $NaBH_4$ (0.005 mol). The reaction was stirred at ambient temperature for 2 h, and then it was poured into water. The aqueous solution was extracted with EtOAc, and the extract was washed (water), dried (magnesium sulfate) and concentrated to afford an oil. The oil was triturated with $Et_2O$ and 1.9 g of a white solid resulted. The solid was dissolved in EtOH and ethereal HCl was added to precipitate a white hydrochloride salt. The salt was recrystallized twice from EtOH to afford the alcohol as a white solid mp 204–206° C.

Analysis: Calculated for $C_{15}H_{18}ClNO_3$: 60.91% C, 6.13% H, 4.74% N. Found: 60.82% C, 6.39% H, 4.68% N.

EXAMPLE 1D

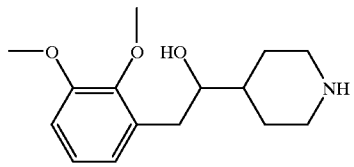

Intermediate: 4-[2-(2,3-Dimethoxyphenyl)-1-hydroxyethyl] piperidine

4-[2-(2,3-dimethoxyphenyl)-1-hydroxyethyl]pyridine (20.0 g, 0.077 mol) in acetic acid (170 ml) over 1.5 g of $PtO_2$ was hydrogenated for 45 minutes on a Parr shaker. The reaction was filtered through Celite and filtrate combined with another run of 21.0 g (0.08 mol). The combined filtrates were concentrated in vacuo and the resulting oil was diluted with water. The aqueous solution was made basic with 50% aqueous NaOH, and the basic mixture extracted with EtOAc. The organic extract was washed with water, dried (magnesium sulfate) and then concentrated to afford 34.3 g of an oil that solidified upon standing. The solid was removed and recrystallized twice from isopropyl ether at 5° C. to afford the piperidine as a white solid, mp 82–84° C.

Analysis: Calculated for $C_{15}H_{23}NO_3$: 67.90% C, 8.74% N. 5.28% N. Found: 67.92% C, 8.77% H, 5.21% N.

EXAMPLE 2A

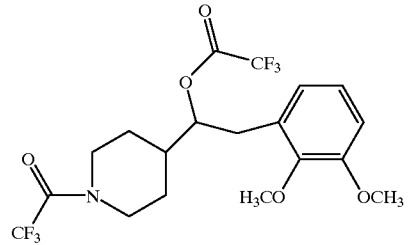

Intermediate: 4-[2-(2,3-Dimethoxyphenyl)-1-(trifluoroacetyloxy)ethyl]-4-piperidine trifluoroacetamide To a stirred solution, under nitrogen of the piperidine alcohol from Example 1D (1.8 g, 6.8 mmol) in $CH_2Cl_2$ (15 ml) was added $Et_3N$ (2.8 ml, 20.4 mmol). The reaction was cooled to about 5° C. (ice bath) and trifluoroacetic anhydride (3.1 g, 2.1 ml, 15 mmol) was added dropwise. After reacting for 1.5 h at ambient temperature, the reaction was concentrated to a yellow oil. This was diluted with water, and extractive workup with $Et_2O$ yielded a yellow oil.

EXAMPLE 2B

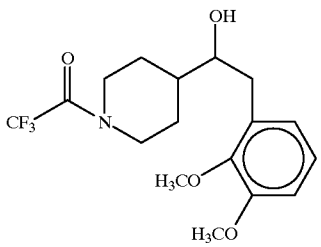

Intermediate: 4-[2-(2,3-Dimethoxyphenyl)-1-hydroxyethyl] piperidine trifluoroacetamide A mixture of 4-[2-(2,3-dimethoxyphenyl)-1-(trifluoro acetyloxy)ethyl]piperidine trifluoroacetamide compound (2.3 g, 6.0 mmol), $K_2CO_3$ (powdered, 1.0 g 6.6 mmol) and anhydrous methanol (15 ml) was stirred at ambient temperature for 3 h. The reaction was filtered and the filtrate concentrated to 2.3 g of a thick, yellow oil. The oil was triturated with $Et_2O$ (a white solid resulted). The solid was filtered, and the filtrate concentrated to afford a thick yellow oil.

EXAMPLE 2C

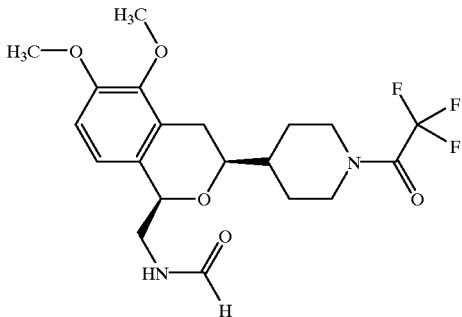

When Formula I is $R_1$=trifluoroacetyl; $R_2$=H; $R_3$=formyl; X and Y=methoxy.

cis-N-[3,4-dihydro-3-(1-trifluoroacetyl-4-piperidinyl)-5,6-dimethoxy-1H-2-benzopyran-1-ylmethyl]formamide To a stirred solution, under nitrogen, of 4-[2-(2,3-dimethoxyphenyl)-1-hydroxyethyl]-1-piperidine trifluoroacetamide (19.7 g, 54 mmol), N-formylaminoacetaldehyde dimethylacetal (8.8 g, 66 mmol) in $CH_2Cl_2$ (150 ml), cooled in an ice bath, was added dropwise $BF_3.O(Et)_2$ (39.4 ml, 320 mmol). The reaction was stirred at ambient temperature for 5.5 h, and then saturated $Na_2CO_3$ was added dropwise until frothing ceased. The organic layer was collected, washed with water, dried ($K_2CO_3$) and was concentrated to afford a yellow oil. The oil was scratched with a glass rod in the presence of ether and a yellow solid was collected. Recrystallization of the sample from IPA-water (twice) yielded a pale yellow solid, mp 165–167° C.

Analysis: Calculated for $C_{20}H_{25}F_3N_2O_5$: 55.81% C, 5.85% H, 6.51% N. Found: 55.86% C, 5.77% H, 6.51% N.

EXAMPLE 2D

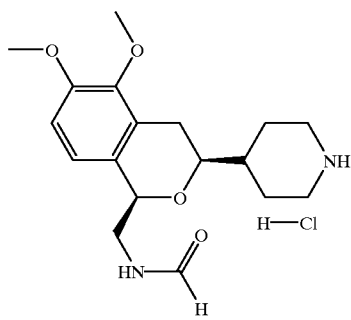

When Formula I is $R_1$=H; $R_2$=H; $R_3$=formyl; X and Y=methoxy. cis-N[-3,4-dihydro-5,6-dimethoxy-3-(4-piperidinyl)-1H-2-benzopyran-1-ylmethyl]Hydrochloride To a stirred mixture of cis-N-[-3,4-dihydro-5,6-dimethoxy-3-(1-trifluoroacetyl-4-piperidinyl)-1H-2-benzopyran-1-ylmethyl]formamide (17.3 g, 40 mmol) in EtOH-THF (100–100 ml), was added slowly, $NaBH_4$ (1.5 g, 40 mmol). The reaction was stirred at ambient temperature, and after about 0.5 h a solution occurred. After reacting for 6 h, the TLC (EtOH—$NH_4OH$, 9:1) indicated some unreacted starting material; therefore an additional amount of $NaBH_4$ (0.33 g 8.7 mmol) was added. The reaction was allowed to proceed for an additional 16 h at ambient temperature, and then it was concentrated in vacuo to a white, tacky solid. The solid was diluted with water, and standard extractive workup with $CH_2Cl_2$ afforded 15.7 g of a white, waxy solid. The solid was dissolved in absolute EtOH (100 ml) and ethereal HCl was added until the solution was acidic. Ether (50 ml) was added and the hydrochloride salt was collected which was recrystallized from EtOH-$Et_2O$ and then from DMF to yield a white solid mp 219–221° C.

Analysis: Calculated for $C_{18}H_{27}ClN_2O_4$: 58.29% C, 7.34% H, 7.55% N. Found: 57.94% C, 7.35% N. 7.76% N.

EXAMPLE 3A

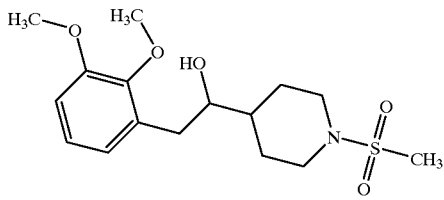

Intermediate: 4-[2-(2,3-Dimethoxyphenyl)-1-hydroxyethyl]-1-piperidine methanesulfonamide A stirred solution of 4-[2-(2,3-dimethoxyphenyl)-1-hydroxyethyl]piperidine (10.0 g, 0.037 mol) and $Et_3N$ (5.7 ml) in $CH_2Cl_2$ (75 ml) was cooled to 5° C. and methanesulfonyl chloride (3.6 g, 0.03 mol) was added dropwise so that the temperature did not rise above 10° C. The reaction was allowed to stand at ambient temperature for 1 h, and the reaction was concentrated in vacuo. The residue was treated with water, resulting in the formation of a white solid, which was collected to afford 10 g of the sulfonamide. The solid was recrystallized from toluene to yield the titled compound, and an additional recrystallization of this, gave 0.8 g of the analytically pure product as a white solid, mp 112–114° C.

Analysis: Calculated for $C_{16}H_{25}NO_5S$: 55.96% C, 7.34% H, 4.08% N. Found: 56.05% C, 7.47% H, 4.27% N.

EXAMPLE 3B

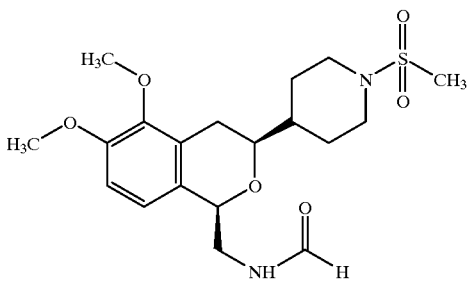

When Formula I is $R_1$=methylsulfonyl; $R_2$=H; $R_3$=CHO; X and Y=methoxy.

cis-N-[3,4-dihydro-5,6-dimethoxy-3-[1-(methylsulfonyl)-4-piperidinyl]-1H-2-benzopyran-1-ylmethyl]formamide A stirred solution, under nitrogen, of 4-[2-(2,3-dimethoxyphenyl)-1-hydroxyethyl]-1-piperidine methanesulfonamide (6.3 g, 0.018 mol) and N-formylacetaldehyde dimethylacetal (3.0 g, 0.022 mol) in $CH_2Cl_2$ (150 ml) was cooled in an ice bath and $BF_3 \cdot O(Et)_2$ (13.1 ml, 0.11 mol) was added dropwise. After complete addition, the reaction was allowed to stand at ambient temperature for 16 h. Saturated $Na_2CO_3$ solution was added carefully, and the organic layer was separated. The organic layer was washed with water, dried ($K_2CO_3$) and the solvent was concentrated to afford a sticky, yellow solid. The solid was triturated with $Et_2O$, and 6.2 g of the slightly yellow solid was collected. The compound was recrystallized from isopropanol to yield 5.8 g (78%) of the benzopyran. A further recrystallization of a 1.5 g sample yielded the titled compound as a white solid, mp 133–135° C.

Analysis: Calculated for $C_{19}H_{28}N_2O_6S$: 55.32% C, 6.84% H, 6.79% N. Found: 55.05% C, 6.61% H, 6.60% N.

EXAMPLE 3C

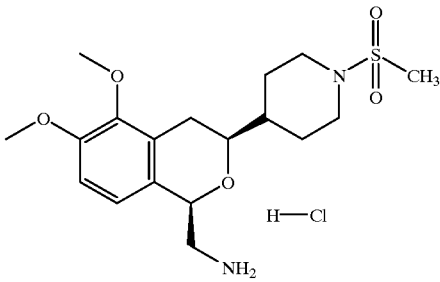

When Formula I is $R_1$=methylsulfonyl; $R_2$ and $R_3$=H; X and Y=methoxy.

cis-1-(Aminomethyl)-3,4-dihydro-5,6-dimethoxy-3-[1-(methylsulfonyl)-4-piperidinyl]-1H-2-benzopyran Hydrochloride A mixture of cis-5,6-dimethoxy-3,4-dihydro-3-(1-methylsulfonyl-4-piperidinyl)-1H-2-benzopyran-1-ylmethyl)formamide (3.8 g, 0.009 mol) and 6N HCl (30 ml) was stirred and refluxed for 2 h, and then permitted to stand at ambient temperature for 16 h. The reaction was diluted with water, cooled in an ice bath and made basic with aqueous NaOH. An off-white solid precipitated from solution and this was collected to afford the desired compound. The compound was dissolved in EtOH and ethereal HCl was added to form a white hydrochloride salt. Recrystallization of the salt, first from EtOH and then from MeOH—$Et_2O$ yielded the amine hydrochloride as a white solid, mp 277–279° C.

Analysis: Calculated for $C_{18}H_{29}ClN_2O_5S$: 51.36% C, 6.94% H, 6.65% N. Found: 51.28% C, 6.72% H, 6.55% N.

EXAMPLE 3D

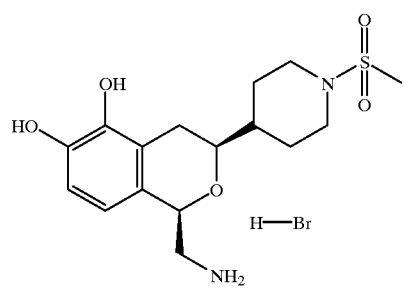

When Formula I is $R_1$=methysulfonyl; $R_2$ and $R_3$=H; X and Y=hydroxy.

cis-1-(Aminomethyl)-3,4-dihydro-3-(1-methylsulfonyl-4-piperidinyl)-1H-2-benzopyran-5,6-diol Hydrobromide This is a demethylation procedure and this compound is made by a similar procedure as described in example 15A starting with cis-1-aminomethyl-3,4-dihydro-5,6-dimethoxy-3-(1-methylsulfonyl-4-piperidinyl)-1H-2-benzopyran. mp 278–280° C. (dec).

Analysis: Calculated for $C_{16}H_{25}BrN_2O_5$: 43.94% C, 5.76% H, 6.41% N. Found: 43.74% C, 5.92% H, 6.19% N.

EXAMPLE 4A

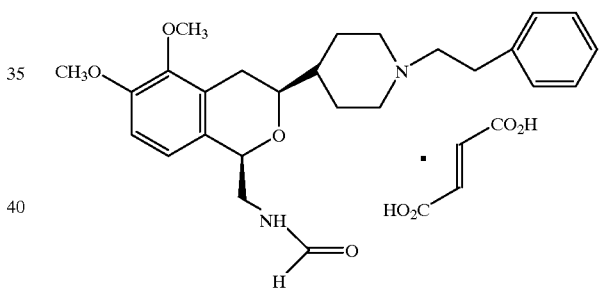

When Formula I is $R_1$=phenethyl (aralkyl); $R_2$=H; $R_3$=formyl; X and Y=methoxy.

cis-N-[-3,4-dihydro-5,6-dimethoxy-3-[1(2-phenylethyl)-4-piperidinyl]-1H-2-benzopyran-1-ylmethyl]fumarate A mixture of cis-N-[-3,4-dihydro-5,6-dimethoxy-3-(4-piperidinyl)-1H-2-benzopyran-1-ylmethyl]formamide (6.0 g, 0.018 mol), $K_2CO_3$ (3.0 g, 0.022 mol), (2-bromoethyl)benzene (3.9 g, 0.021 mol) and $CH_3CN$ (125 ml) was stirred at reflux under nitrogen for 1 h and then at ambient temperature for 18 h. The reaction was filtered and the filtrate was concentrated to yield 7.6 g of a light yellow oil. The compound was purified by preparative HPLC (Water's Associates Prep LC/System 500) using 2 silica gel columns and 4% $Et_2NH$-EtOAc as eluent to afford a white foam which was dissolved in EtOAc (20 ml) and the solution was stirred at reflux. A solution of fumaric acid (0.12 g, 1.0 mmol) in hot 25% MeOH-EtOAc (4 ml) was added. The suspension was cooled and filtered to provide the fumarate salt. Recrystallization from $CH_3CN$ gave a white solid, mp 192–194° C.

Analysis: Calculated for $C_{30}H_{38}N_2O_8$: 64.97% C, 6.91% H, 5.05% N. Found: 64.98% C, 7.07% H, 5.00% N.

EXAMPLE 4B

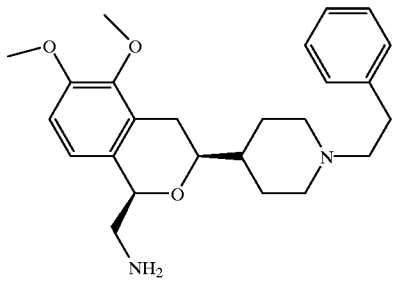

When Formula I is $R_1$=phenethyl; $R_2$ and $R_3$=H; X and Y=methoxy.
cis-1-(Aminomethyl)-3,4-dihydro-5,6-dimethoxy-3-[1(2-phenylethyl)-4-piperidinyl]-1H-2-benzopyran A mixture of cis-N-[3,4-dihydro-5,6-dimethoxy-3-[1-(2-phenylethyl)-4-piperidinyl]-1H-2-benzopyran-1-ylmethyl] formamide hydrochloride (4.7 g, 10 mmol) and its free base (2.1 g, 4.7 mmol) was dissolved in 3N HCl (30 ml)-EtOH (30 ml), and refluxed for 2 h. The reaction was diluted with water, and then stirred and cooled in an ice bath, while 50% aqueous NaOH was added dropwise. A white solid separated from solution and this was collected to afford the titled compound. The compound was recrystallized from toluene to afford the amine as a white solid, mp 100–102° C.

Analysis: Calculated for $C_{25}H_{34}N_2O_3$: 73.14% C, 8.35% H, 6.82% N. Found: 72.93% C, 8.56% H, 6.72% N.

EXAMPLE 4C

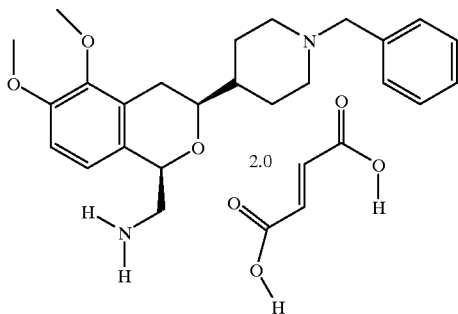

When Formula I is $R_1$=benzyl; $R_2$ and $R_3$=H; X and Y=methoxy.
cis-1-(Aminomethyl)-3,4-dihydro-5,6-dimethoxy-3-(1-benzyl-4-piperidinyl)-1H-2-benzopyran Difumarate This is the benzyl form of example 4B which has been converted to a difurmarate salt. It is prepared by a similar procedure as example 4A and 4B starting from cis-N[-3,4-dihydro-5,6-dimethoxy-3-(benzyl-4-piperidinyl)-1H-2-benzopyran-1-ylmethyl]formamide.

The compound was dissolved in warm EtOAc (200 ml) and filtered. The warm filtrate was treated with a hot solution of fumaric acid (2.05 g, 17.7 mmol) dissolved in 50% MeOH-EtOAc (25 ml) and the salt precipitated as a tacky solid. After cooling to ambient temperature, scratching produced a white solid which was recrystallized from EtOH to afford a white solid. Recrystallization twice from EtOH provided the difumarate salt as a white solid, mp=145–147° C.

Analysis: Calculated for $C_{32}H_{40}N_2O_{11}$: 61.14% C, 6.41% H, 4.46% N. Found: 61.05% C, 6.83% H, 4.66% N.

EXAMPLE 4D

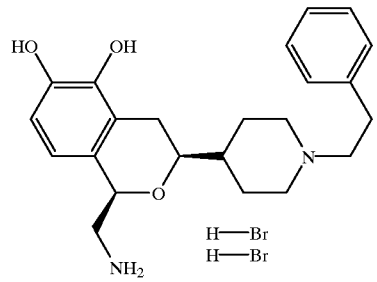

When Formula I is $R_1$=phenethyl; $R_2$ and $R_3$=H; X and Y=OH.
cis-1-(Aminomethyl)-3,4-dihydro-3-[1-(2-phenylethyl)-4-piperidinyl]-1H-2-benzopyran-5,6-diol Dihydrobromide Sesquihydrate To stirred solution of cis-1-(aminomethyl)-3,4-dihydro-5,6-dimethoxy-3-[1-(2-phenethyl)-4-piperidinyl]-1H-2-benzopyran (2.5 g, 1.1 mmol in $CH_2Cl_2$ (30 ml), under nitrogen, cooled to −78° C. was added, dropwise, 1M $BBr_3$ in $CH_2Cl_2$ (31 ml, 31 mmol). After complete addition, the reaction was stirred at −78° C. for 3 h, and then at −10° C. for 1 h. The reaction was cooled once again to −78° C. and methanol (30 ml) was added dropwise. The cooling bath was removed, and the solvent was concentrated under reduced pressure to yield a white solid. This solid was triturated with methanol (30 ml), and the methanol was removed in vacuo. This operation was repeated once more and the resultant solid was triturated with EtOH and collected to afford the titled compound which was recrystallized twice from MeOH-$Et_2O$ and once from methanol to afford a white solid. This solid was dried at 110° C. and high vacuum for 2.5 h and yielded the catechol as a dihydrobromide sesquihydrate, mp 188–190° C.

Analysis: Calculated for $C_{23}H_{30}N_2O_3 \cdot 2HBr \cdot 1.5H_2O$ 48.34% C, 6.17% H, 4.90% N. Found: 48.52% C, 6.26% H, 4.88% N.

EXAMPLE 4E

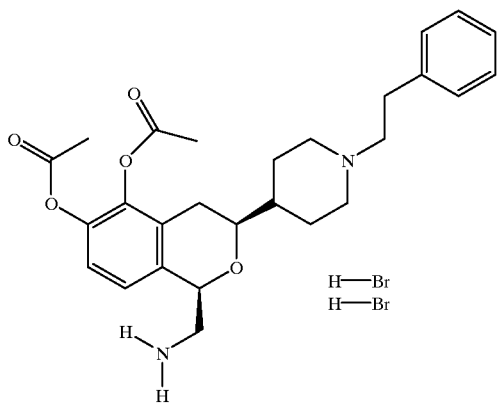

When Formula I is $R_1$=phenethyl; $R_2$ and $R_3$=H; X and Y=acyloxy.
cis-1-(Aminomethyl)-5,6-diacetoxy-3,4-dihydro-3-[1-(2-phenylethyl)-4-piperidinyl]-1H-2-benzopyran Dihydrobromide To a stirred solution of cis-1-(aminomethyl)-3,4-dihydro-3-[1-(2-phenethyl)-4-piperidinyl]-1H-2-benzopyran-5,6- diol dihydrobromide (5.0 g, 9.2 mmol) in CF₃CO₂H (40 ml) under nitrogen at ambient temperature was added, dropwise, acetyl bromide (1.5 ml, 20.3 mmol) over 10 minutes. After complete addition, the reaction was stirred at ambient temperature for 90 minutes. Water (4 drops) was added and the reaction was concentrated to afford 8.3 g of a gummy beige residue. The crude product was dissolved in warm IPA (25 ml) and filtered. The filtrate was stirred under nitrogen until it was cooled and Et₂O (100 ml) was added to precipitate a white solid. The suspension was stirred for 2 h under nitrogen and the solid was collected to yield 7.0 g. The compound was recrystallized twice from MeOH-Et₂O to give a white solid. This was combined with two additional samples (8.3 g total), and recrystallization from MeOH-Et₂O provided the compound which was dried at 110° C. under high vacuum for 3 h to yield a white solid mp 190–193° C.

Analysis: Calculated for $C_{37}H_{36}Br_2N_2O_5$ 51.61% C, 5.77% H, 4.46% N. Found: 51.70% C, 5.80% H, 4.42% N.

EXAMPLE 5

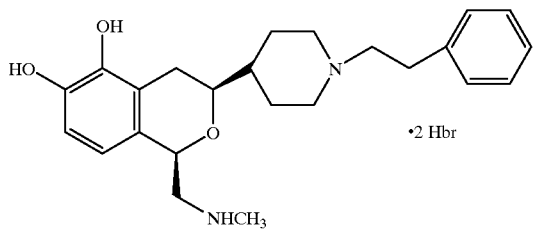

When Formula I is $R_1$=phenethyl; $R_2$=H; $R_1$=$CH_3$; X and Y=hydroxy.
cis-1-(N-Methylaminomethyl)-3,4-dihydro-3-[1-(2-phenylethyl)-4-piperidinyl)-1H-2-benzopyran-5,6-diol Dihydrobromide This is the monoalkylated form of example 4D and may be made according to a similar procedure starting from cis-1-(N-methylaminomethyl)-3,4-dihydro-5,6-dimethoxy-3-[1-(2-phenylethyl)-4-piperidinyl]-1H-2-benzopyran (3.2 g, 7.5 mmol). mp 208–211° C.

Analysis: Calculated for $C_{24}H_{36}Br_2N_3$: 51.63% C, 6.14% H, 5.02% N. Found: 51.67% C, 6.16% H, 4.93% N.

EXAMPLE 6

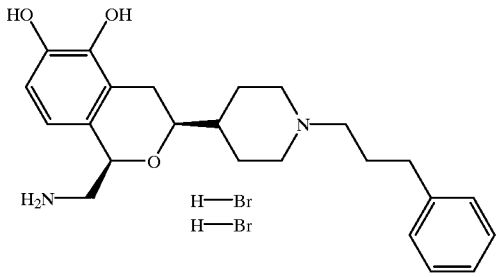

When Formula I is $R_1$=phenylpropyl; $R_2$ and $R_3$=H; X and Y=OH.
cis-1-(Aminomethyl)-3,4-dihydro-3-[1-(3-phenylpropyl)-4-piperidinyl]-1H-2-benzopyran-5,6-diol Dihydrobromide Hemihydrate This is the phenylpropyl form of example 4D and is made by a similar procedure starting from cis-1-(aminomethyl)-3,4-dihydro-5,6-dimethoxy-3-[1-(3-phenylpropyl)-4-piperidinyl]-1H-2-benzopyran (1.6 g, 37 mmol). mp 263–265° C.

Analysis: Calculated for $C_{24}H_{34}Br_2N_{20}O_3 \cdot 0.5H_2O$: 50.80% C, 6.21% H, 4.94% N. Found: 50.97% C, 6.33% H, 4.77% N.

EXAMPLE 7

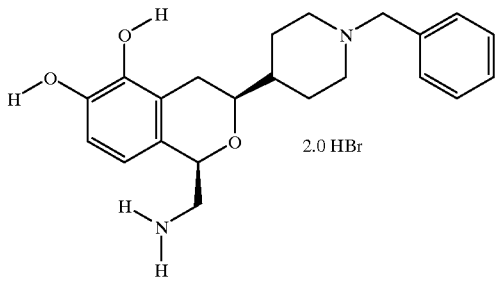

When Formula I is $R_1$=benzyl; $R_2$ and $R_3$=H; X and Y=hydroxy.

cis-1-(Aminomethyl)-3,4-dihydro-3-(1-benzyl-4-piperidinyl)-1H-2-benzopyran-5,6-diol Dihydrobromine This is the benzyl form of example 4D and is made by a similar procedure starting from cis-1-(aminomethyl)-3,4-dihydro-5,6-dimethoxy-3-(1-benzyl-4-piperidinyl)-1H-2-benzopyran (2.2 g, 5.5 mmol). mp 210–213° C.

Analysis: Calculated for $C_{22}H_{30}Br_2N_2O_3$: 49.83% C, 5.70% H, 5.28% N. Found: 49.86% C, 5.58% H, 5.15% N.

EXAMPLE 8

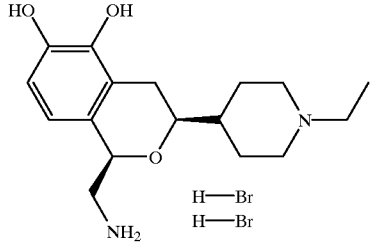

When Formula I is $R_1$=ethyl; $R_2$ and $R_3$=H; X and Y=OH.

cis-1-(Aminomethyl)-3,4-dihydro-3-(1-ethyl-4-piperidinyl)-1H-2-benzopyran-5,6-diol Dihydrobromide This is a demethylation procedure (at positions X and Y of Formula I) which is performed similarly to the procedure described in example 4D starting from cis-1-(aminomethyl)-3,4-dihydro-3-(1-ethyl-4-piperidinyl)-5,6-dimethoxy-1H-2-benzopyran (2.0 g, 5.8 mmol). mp 302–304° C. (gas evolution).

Analysis: Calculated for $C_{17}H_{28}Br_2N_2O_3$: 43.61% C, 6.03% H, 5.98% N. Found: 43.67% C, 6.17% H, 5.93% N.

EXAMPLE 9

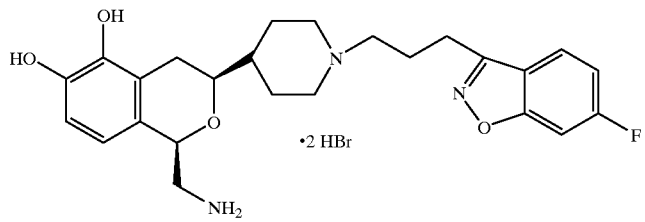

When Formula I is $R_1$=optionally substituted heteroaryl alkyl; $R_2$ and $R_3$=H; X and Y=OH.

cis-1-(Aminomethyl)-3,4-dihydro-3-[1-[3-(6-fluoro-1,2-benzisoxazol-3-yl)propyl]piperidin-4-yl]-1H-2-benzopyran-5,6-diol Dihydrobromide N-(4-Pyridylmethyl)isocyanide is made from 4-aminomethyl pyridine (Aldrich) which is reacted with ethylformate to form N-(4-pyridylmethyl)formamide according to the method in *Liebigs Ann. Chem.* 1976, 969–977. Triphenylphosphine and triethylamine are reacted with 4-[N-methylformamide]pyridine in the presence of carbon tetrachloride and dichloromethane to produce the N-(4-pyridylmethyl)isocyanide.

The N-(4-pyridylmethyl)isocyanide is condensed with 2,3-dimethoxybenzaldehyde (Aldrich) to form N-[2-(2,3-dimethoxyphenyl)-1-(4-pyridinyl)vinyl]formamide according to the method of example 1A. The 2-(2,3-dimethoxyphenyl)-1-(4-pyridinyl)ethanone is made according to the method of example 1B. The 4-[2-(2,3-dimethoxyphenyl)-1-hydroxyethyl]pyridine is made according to the method of example 1C. The 4-[2-(2,3-dimethoxyphenyl)-1-hydroxyethyl]piperidine is made according to the method of example 1D. The 4-[2-(2,3-dimethoxyphenyl)-1-(trifluoroacetyloxy)ethyl]-4-piperidine trifluoroacetamide is made according to the method of example 2A. The 4-[2-(2,3-dimethoxyphenyl)-1-hydroxyethyl]piperidine is made according to the method of example 2B. The cis-5,6-dimethoxy-3,4-dihydro-1-(N-formylamionmethyl)-3-(1-trifluoroacetyl-4-piperidinyl)-1H-2-benzopyran is made according to the method of example 2C. The cis-1-(N-formylaminomethyl)-3,4-dihydro-5,6-dimethoxy-3-(4-piperidinyl)-1H-2-benzopyran is made according to the method of example 2D.

Cis-1-(N-formylaminomethyl)-3,4-dihydro-5,6-dimethoxy-3-(4-piperidinyl)-1H-2-benzopyran (6.0 g, 0.018 mol), $K_2CO_3$ (3.0 g, 0.022 mol) and 1-chloro-3-(6-fluorobenzo[d]isoxazol-3-yl)-propane] (6.2 g, 0.029 mol) and $CH_3CN$ (125 ml) was stirred at reflux uner $N_2$ for 6.5 hours and allowed to stand at room temperature for 3.5 days; refluxing was resumed for 4.0 hours. An additional 1.0 g $K_2CO_3$ was added and refluxed for 18 hours. The reaction was cooled and filtered. The filtrate was concentrated to yield 12.1 g of a thick clear brown oil and purified by silica gel columns eluting with $Et_2NH$-EtOAc at 200 mls/min. to provide cis-N-[3,4-dihydro-5,6-dimethoxy-3-[1-[3-(6-fluoro-1,2-benzisoxazol-3-yl)propyl]-4-piperidinyl]-1H-2-benzopyran-1-ylmethyl]formamide.

To the foregoing compound (5.5 g, 10.8 mmol), 3N HCl (30 ml) and absolute EtOH (30 ml) was stirred at reflux for 4.5 hours. The reaction was cooled to room temperature, diluted with water (50 ml) and cooled in an ice bath. 50% NaOH (10 ml) was added dropwise and initially a white solid formed at pH 7–8; however upon further basification, an oil precipitated out of the aqueous mix. The oil was extracted into $CH_2Cl_2$ (3×100 ml). The $CH_2Cl_2$ extract was washed with water(50 ml), dried with $MgSO_4$ and concentrated to yield 5.7 g of cis-1-aminomethyl-3,4-dihydro-5,6-dimethoxy-3-[1-[3-( 6-fluoro-1,2-benzisoxazol-3-yl) propyl]-4-piperidinyl]-1H-2-benzopyran.

To a stirred solution of cis-1-aminomethyl-3,4-dihydro-5,6-dimethoxy-3-[1-[3-(6-fluoro-1,2-benzisoxazol-3-yl) propyl]-4-piperidinyl]-1H-2-benzopyran (2.4 g, 5.2 mmol) in $CH_2Cl_2$ (32 ml) under nitrogen and cooled to $-78°$ C. was added, dropwise, $BBr_3$ (2.6 ml, 27.5 mmol) in $CH_2Cl_2$ (5 ml). After complete addition the reaction was stirred at $-78°$ C. for 3 h and then at $-20°$ C. for 1 h. The reaction was cooled at $-78°$ C. and anhydrous methanol (32 ml) was added dropwise. The solution was concentrated to yield a damp beige solid. The solid was triturated with anhydrous methanol (40 ml) and the volatiles were removed in vacuo to yield a tacky beige solid. This process was repeated once again and the resultant beige solid was diluted with absolute ethanol (30 ml). The mixture was heated on a steam bath until dissolution occurred and the solution was stirred under nitrogen for 18 h. The resultant product was collected as a white solid. Two recrystallizations from MeOH-$Et_2O$ provided the dihydrobromide salt. This compound was dried under high vacuum at $111°$ C. for 3 h to yield a white solid that contained about 1.5% water. mp 188–190° C.

Analysis: Calculated for $C_{25}H_{32}Br_2FN3O_4$: 48.64% C, 5.22% H, 6.81% N. Found: 48.77% C, 5.53% H, 6.70% N.

EXAMPLE 10

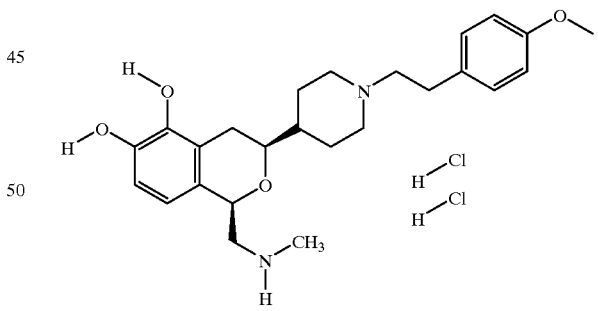

When Formula I is $R_1$=arylalkyl substituted with methoxy; $R_2$=H, $R_3$=$CH_3$; X and Y=OH.

cis-3,4-Dihydro-3-[1-[2-(4-(4-methoxyphenyl)ethyl]-4-piperidinyl]-1-(N-methylaminomethyl)-1H-2-benzopyran-5,6-diol Dihydrochloride Lithium aluminum hydride (0.073 g, 1.9 mmol) was added to a stirred solution of cis-N-[5,6-(cyclohexylidenedioxy)-3,4-dihydro-3-[1-[2-(4-methoxyphenyl)ethyl]-4-piperidinyl]-1H-2-benzopyran-1-ylmethyl]formamide (0.500 g, 0.96 mmol) in tetrahydrofuran (10 ml) at room temperature. After heating under reflux for 1 h, the reaction was quenched with water and saturated ammonium chloride solution, and diluted with ether. The solvent was removed in vacuo to a colorless oil. This product was then added to a 5M solution of concentrated HCl in ethanol (8 ml) at room temperature. After heating under reflux for 1 h, a white solid precipitated out of solution. The solid was collected by filtration and dried at 80° C. for 5 h to yield a solid, mp 230–232° C.

Analysis: Calc. for $C_{25}H_{36}Cl_2N_2O_4$: 60.12 % C, 7.26 % H, 5.61 % N. Found: 59.73 % C, 7.40 % H, 5.55 % N.

EXAMPLE 11

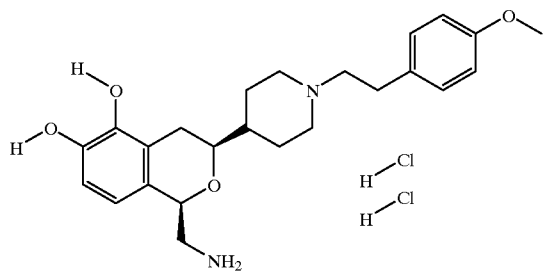

When Formula I is $R_1$=arylalkyl substituted with methoxy; $R_2$ and $R_3$=H; X and Y=OH.

cis-1-(Aminomethyl)-3,4-dihydro-3-[1-[2-(4-methoxyphenyl)ethyl]-4-piperidinyl]-1H-2-benzopyran-5,6-diol Dihydrochloride A 15% aqueous NaOH solution (15 ml) was added to cis-N-(5,6-cyclohexylidenedioxy)-3,4-dihydro-3-[1-[2-(4-methoxyphenyl)ethyl]4-piperidinyl]-1H-2-benzopyran-1-ylmethyl)formamide (1.20 g, 0.0023 mole) at room temperature. After stirring under reflux for 1 h, the mixture was diluted with water and extracted into ethyl acetate. The solvent was concentrated in vacuo to yield an orange oil 1.08 g (95%). This product was then added to a 5M solution of concentrated HCl in ethanol (20 ml) at room temperature. After stirring under reflux for 0.5 h, a pale yellow solid precipitated out of solution. The solid was collected and dried at 80° C., under vacuum, for 5 h, mp 315–317° C.

Analysis: Calc. for $C_{24}H_{34}Cl_2N_2O_4$: 59.38 % C, 7.06 % H, 5.77 % N. Found: 59.09 % C, 7.18 % H, 5.73 % N.

EXAMPLE 12

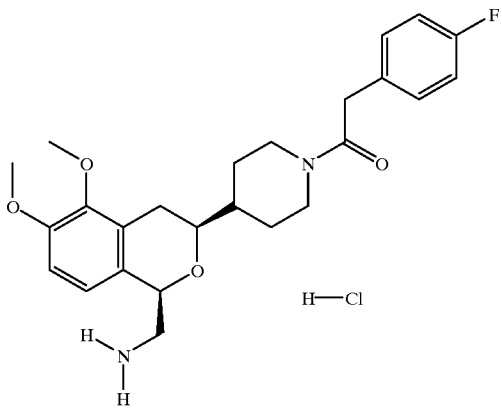

When Formula I is $R_1$=C(=O)CH$_2$-phenyl substituted with fluoro; $R_2$ and $R_3$=H; X and Y=H.

1-[2-(Fluorophenyl)acetyl]-H-[3,4-dihydro-5,6-dimethoxy-1-(aminomethyl)-1H-2-benzopyran-3-yl]piperidine Hydrochloride A solution of cis-N-[3-[1-[2-(4-fluorophenyl)acetyl]-4-piperidinyl]-3,4-dihydro-5,6-dimethoxy-1H-2-benzopyran-1-ylmethyl]formamide (11.5 g, 0.024 mol), 3.0 N HCl (60 ml) and EtOH (60 ml) was stirred at reflux for 4.5 h. The reaction was cooled to ambient temperature and was diluted with water (100 ml). The solution was cooled to 5° C. and 50% NaOH was added to make it basic. The flask was stored at 4° C. for 18 h and a brown oil separated. Most of the aqueous was decanted away and the oil was extracted into CHCl$_3$. The CHCl$_3$ extract was washed with water, dried with magnesium sulfate and concentrated to yield 10.5 g of an off-white gum. The product was dissolved in Et$_2$O (500 ml) and some foreign material was filtered away. The filtrate was treated with 1.0 M Et$_2$O-HCl to make the solution pH=1. The resultant suspension was stirred for 30 minutes and the solid was collected to yield 9.4 g of a white solid. The solid was triturated with boiling CH$_3$CN (40 ml) for about 10 minutes and allowed to cool to ambient temperature. The solid was filtered and dried to afford 8.3 g. Recrystallization from ethanol gave 3.8 g of a white solid. The filtrate was concentrated to about ⅓ the volume and cooled to ambient temperature to produce an additional 3.1 g of material. The two samples were combined and suspended in water (100 ml) and aqueous NaOH was added to make the mixture basic. This was extracted with CH$_2$Cl$_2$ and the CH$_2$Cl$_2$ extract was washed with water, dried with magnesium sulfate and concentrated to yield 6.2 g of a white foam. Purification via preparative HPLC (Waters Prep LC2000, using 2 silica gel columns and 0.5% NH$_4$OH-7% MeOH-CH$_2$Cl$_2$ as eluent) provided a white foam which was dissolved in Et$_2$O (25 ml) and filtered. The filtrate was treated with 1.0 M Et$_2$O-HCl to precipitate a white solid that was collected. Recrystallization from ethanol gave a hydrochloride salt as a white solid mp 229–231° C.

Analysis: Calculated for $C_{25}H_{32}ClFN_2O_4$: 62.69% C, 6.73% H, 5.85% N. Found: 62.49% C, 6.67% H, 5.77% N.

EXAMPLE 13

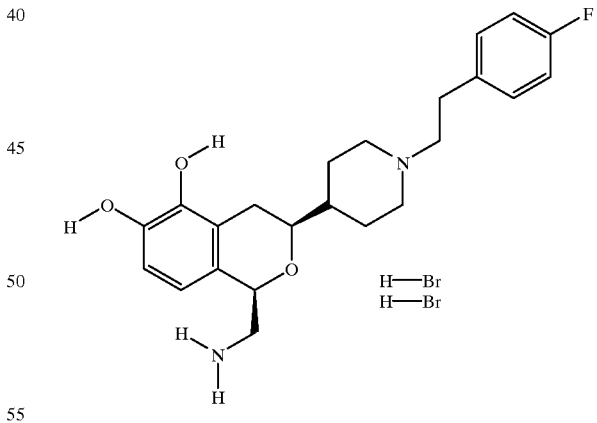

When Formula I is $R_1$=substituted phenethyl; $R_2$ and $R_1$=H; X and Y=hydroxy.

cis-1-(Aminomethyl)-3,4-dihydro-3-[1-[2-(4-fluorophenethyl)]-4-piperidinyl]-1H-2-benzopyran-5,6-diol Dihydrobromide This is a demethylation procedure (at positions X and Y of Formula I) and this compound may be prepared by a similar procedure as described in example 4D starting from cis-(aminomethyl)-3,4-dihydro-5,6-dimethoxy-3-[1-[2-(4-fluorophenethyl)]-4-piperidinyl]-1H-2-benzopyran (2.0 g, 4.7 mmol). mp 182–185° C.

Analysis:
Calculated for $C_{23}H_{31}Br_2FN_2O_3$: 49.13% C, 5.56% H, 4.98% N. Found: 49.28% C, 5.50% H, 4.95% N.

EXAMPLE 14

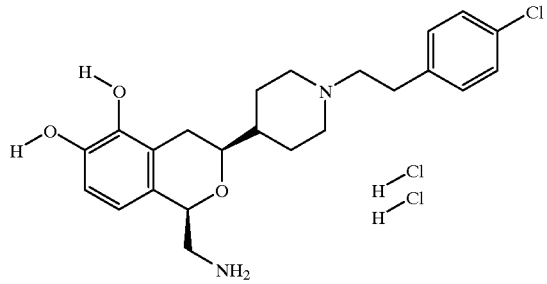

When Formula I is $R_1$=arylalkyl substituted with Cl; $R_2$ and $R_3$=H; X and Y=OH.
cis-1-(Aminomethyl)-3-[1-[2-(4-chlorophenyl) ethyl]-3,4-dihydro-4-piperidinyl]-1H-2-benzopyran-5,6-diol dihydrochloride A 15% aqueous NaOH solution (15 ml) was added to cis-N-(5,6-cyclohexylidenedioxy-3-[1-[2-(4-chlorophenyl) ethyl]-4-piperidinyl]-3,4-dihydro-1H-2-benzopyran-1-ylmethyl)formamide (1.30 g, 0.0025 mole) at room temperature. After stirring under reflux for 1 h, the mixture was diluted with water and extracted into ethyl acetate. The solvent was concentrated in vacuo to yield an orange oil. This product was then added to a 5M solution of concentrated HCl in ethanol (20 ml) at room temperature. After stirring under reflux for 0.5 h, a pale yellow solid precipitated out of solution. The solid was collected and dried at 80° C. for 5 h, m.p. 325–326° C.

Analysis: Calc. for $C_{23}H_{31}Cl_3N_2O_3$ 56.39 % C, 6.38 % H, 5.72 % N. Found: 56.11 % C, 6.39 % H, 5.56 % N.

EXAMPLE 15

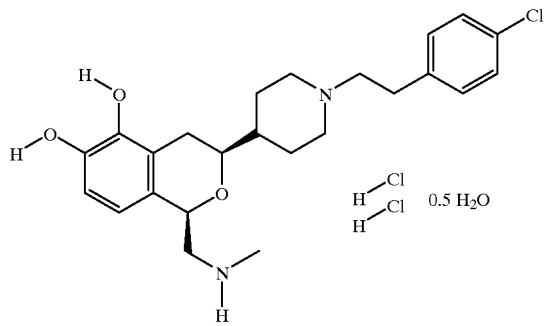

When Formula I is $R_1$=arylalkyl substituted with Cl; $R_2$=H; $R_3$=CH$_3$; X and Y=OH.
cis-3-[1-[2-(4-Chlorophenyl)ethyl]-4-piperidinyl]-3,4-dihydro-1-(N-methylaminomethyl)-1H-2-benzopyran-5,6-diol dihydrochloride hemihydrate Lithium aluminum hydride (0.072 g, 0.0019 mole) was added to a stirred solution of cis-N-(5,6-cyclohexylidenedioxy)-3-[1-[2-(4-chlorophenyl)ethyl]-4-piperidinyl]-3,4-dihydro-1H-2-benzopyran-1-ylmethyl) formamide (0.500 g, 0.00095 mole) at room temperature. After heating under reflux for 2 h, the reaction was quenched with water and saturated ammonium chloride solution, and diluted with ether. The organic layer was separated and the solvent was removed in vacuo to yield 0.390 g (80%) of a colorless oil. This product was then added to a 5M solution of concentrated HCl in ethanol (8 ml) at room temperature. After heating under reflux for 1 h, a white solid precipitated out of solution. The solid was collected by filtration and dried at 80° C. for 5 h to yield a solid, m.p. 318–320° C.

Analysis: Calc. for $C_{24}H_{33}C N_2O_3.0.5H_2O$: 56.20 % C, 6.68 % H, 5.46 % N. Found 56.03 % C, 6.61 % H, 5.48 % N.

EXAMPLE 16

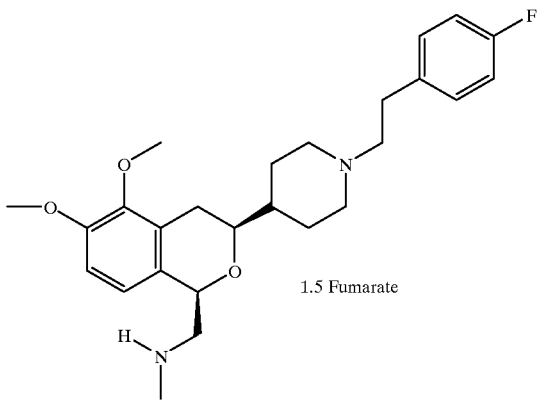

When Formula I is $R_1$=substituted phenethyl; $R_2$=H; $R_3$=methyl; X and Y=methoxy.

cis-3,4-dihydro-5,6-dimethoxy-3-[1-[2-(4-fluorophenethyl)]-4-piperidinyl]-1-(N-methylaminomethyl)-1H-2-benzopyran Sesquifumarate To a stirred solution of cis-N-[3-[1-[2-(4-fluorophenyl) acetyl]-4-piperidinyl]-3,4-dihydro-5,6-dimethoxy-1H-2-benzopyran-1-ylmethyl]formamide (7.2 g, 0.015 mol) in THF (250 ml) under nitrogen and cooled in an ice bath was added, dropwise, LAH/THF (40.0 ml of an 1.0 M solution) over 20 minutes. After complete addition, the reaction was stirred at reflux for 1.5 h. The reaction was cooled in an ice bath and water (5 ml) was added dropwise followed by 1.0 M NaOH (2 ml). The mixture was filtered and the filtrate was concentrated to yield 6.6 g of a brown oil. The oil (6.4 g, 0.014 mol) was dissolved in ethanol (80 ml) and filtered. The filtrate was stirred and warmed and a hot slurry of fumaric acid (3.4 g 0.029 mol) in ethanol (20 ml) was added. The solution was refluxed briefly and then stirred at ambient temperature under nitrogen for 20 h. The resultant product was collected to afford 8.0 g of a beige solid. Recrystallization from ethanol gave an off-white solid. An appreciable amount of solid did not dissolve during this process therefore it was collected to provide an additional 2.1 g of a white solid that appeared to be of the same quality as the recrystallized material which was recrystallized from ethanol to afford the sesquifumarate salt as a white solid mp 118–120° C.

Analysis: Calculated for $C_{32}H_{41}FN_2O_9$: 62.31% C, 6.71% H, 4.54% N. Found: 62.71% C, 6.95% H, 4.76% N.

EXAMPLE 17

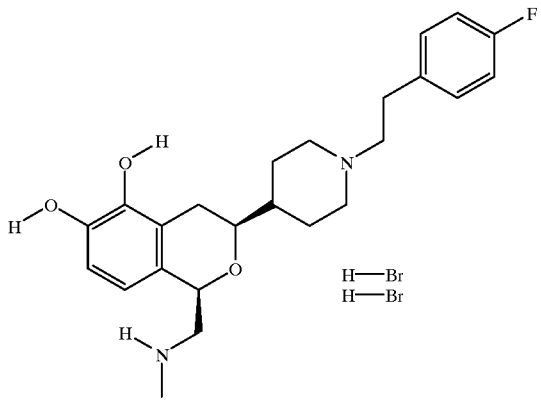

When Formula I is R₁=aralkyl substituted with F; R₂=H; R₃=CH₃; X and Y=OH.
cis-3,4-dihydro-3-[1-[2-(4-fluorophenethyl) 1 -4-piperidinyl]1-(N-Methylaminomethyl)-1H-2-benzopyran-5,6-diol Dihydrobromide This is a demethylation procedure (at positions X and Y of Formula I) and the compound may be made by a similar procedure as described in example 5 starting with cis-1-(N-methylaminomethyl)-3,4-dihydro-5,6-dimethoxy-3-[1-[2-(4-fluorophenethyl)]-4-piperidinyl]-1H-2-benzopyran. mp 216–218C.°.

Analysis: Calc. for $C_{24}H_{33}Br_2FN_2O_3$: 50.02 % C, 5.77 % H, 4.86 % N. Found: 50.15 % C, 5.74 % H, 4.69 % N.

EXAMPLE 18A

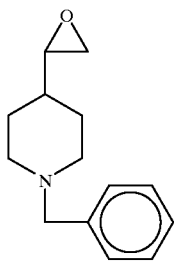

Intermediate: 1-Benzyl-4-oxiranylpiperidine

A slurry of 4-piperidinyl ethyl ester (6.36 mol), K₂CO₃ (10.98 mol) and benzyl chloride (7.63 mol) in ethanol (5 L) was stirred at room temperature under nitrogen for forty-eight hours. The pale yellow slurry was filtered through celite. The filtrate was concentrated to an orange oil which was stirred with EtOAc (3 L) and H₂O (1.5 L) for five minutes. The organic layer was isolated, washed with H₂O (2×500 mL) and brine (1×500 ml) dried (MgSO₄) and filtered. The filtrate was concentrated to give ethyl N-benzyl isonipecotate as an orange oil.

LAH (1M solution in THF, 4.37 mol) was diluted with THF (4 L), the solution was chilled to 0° C. via IPA/dry-ice bath, under nitrogen. A solution of ethyl N-benzyl isonipecotate (2.95 mol) in THF (4 L) was added over two hours. The cold bath was removed and the solution was stirred for three hours before heating at reflux for eighteen hours. The heating mantle was removed and the solution was stirred at room temperature for eighteen hours before being quenched at 0° C. by the dropwise addition of: EtOAc (110 mL), H₂O (164 mL), 10% aqueous sodium hydroxide (246 mL) and H₂O (410 mL). The slurry was stirred at room temperature for eighteen hours and filtered which provided N-Benzyl-4-hydroxymethylpiperidine.

A solution of DMSO (7.78 mol) in dichloromethane (3 L) was added dropwise to a solution of oxalyl chloride (3.54 mol) (1.77 L of 2M solution in CH₂CL₂) at –65° C. over a 1.75 hour period. After stirring for 25 minutes, a solution of N-benzyl-4-hydroxymethylpiperidine in CH₂Cl₂ (1L) was added at –65° C. over a 1.5 hour period. After stirring for 20 minutes, Et₃N (10.43 mol) was added over 30 minutes. The cold bath was removed and the beige slurry was stirred to room temperature over eighteen hours before adding water (7.5 L). This mixture was stirred for 10 minutes. The aqueous layer was isolated and extracted with Et₂O (2×4 L, then 1×2 L). The organic layers were combined, washed with water (1×2 L) and brine (2×2 L), dried (MgSO₄) and filtered. The clear orange filtrate was concentrated to give a crude brown oil which was purified by gravity filtration through SiO₂, eluting with heptane followed by EtOAc. Fractions were collected and concentrated to provide N-benzyl-4-piperidinyl carboxaldehyde.

At room temperature, under nitrogen, a solution of KOt-Bu (95%, 2.24 mol) in four liters of DMSO was added dropwise to a solution of (CH₃)₃SOI (98%, 2.24 mol) in four liters of DMSO over forty minutes. The clear yellow solution was heated at 50° C. for 3.5 hours and then a solution of N-benzyl-4-piperidinyl carbaldehyde (1.72 mol) in 1.5 liters of DMSO was added over 10 minutes. Heating at 50° C. was continued for one hour, then the solution was stirred at room temperature for eighteen hours. The solution was poured into ice-water (9 L) and extracted with heptane (6×2 L). The extracts were combined, washed with water (2×2 L), dried (MgSO₄), filtered, and concentrated (40° C./50 torr) to a clear orange oil The oil was purified by gravity filtration through SiO₂ (5 L) eluting with EtOAc (12 L). Fractions were combined and concentrated to give the titled compound as a clear yellow oil.

EXAMPLE 18B

Intermediate: spiro[(1,3-benzodioxole)-2,1-cyclohexane]

A mixture of 1,2-dihydroxybenzene (2.72 mol), cyclohexanone (2.72 mol), toluene (2.3 L) and p-TsOH (0.55 g) was refluxed under nitrogen for eighteen hours. A total of 48 mL water was collected with a Dean-Stark trap After cooling, the mixture was neutralized with 5% NaOH, washed with water, dried (MgSO₄) and filtered. The filtrate was concentrated to give a crude gold oil which solidified upon standing. The crude solid was recrystallized from pet. Ether (400 mL, boiling range 35–60° C.) to give the spirol ketal.

EXAMPLE 19

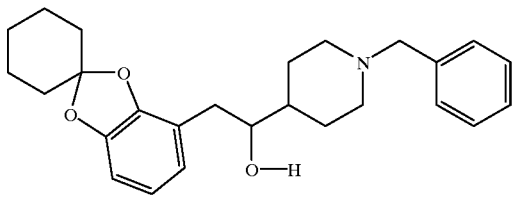

Intermediate: 2-(1-Benzyl-4-piperidinyl)-1-spiro(1,3-benzodioxole-2,1'-cyclohexane)-2-ethanol To a stirred solution of spiro[(1,3-benzodioxole)-2,1'-cyclohexane] (5.5 g, 0.029 mol) in THF (40 ml) under $N_2$ at −3° was added, dropwise, n-butyllithium (14 ml of a 2.5M n-BuLi/hexanes solution, 0.035 mol) over 10 minutes. After complete addition, the reaction was stirred at ambient temperature for 4 hours. The reaction was cooled to −3° and a solution of 1-benzyl-4-oxiranylpiperidine (5.9 g, 0.027 mol) in THF (10 ml) was added dropwise over 10 minutes. After complete addition the reaction was warmed to ambient temperature and stirred for 17 hours. The reaction was poured into saturated $NH_4Cl$ (about 70 ml) and the aqueous solution was extracted with $Et_2O$ (3×75 ml). The $Et_2O$ extract was washed with aqueous $NH_4Cl$, washed with saturated NaCl, dried with $MgSO_4$ and concentrated to yield 12.0 g of a viscous red oil. The titled compound was isolated via preparative HPLC (Waters Prep LC 2000, using 2 silica gel columns and 5% MeOH-$CH_2Cl_2$ as eluent) to yield a beige solid which was recrystallized from ethanol to afford a white solid which was recrystallized again from ethanol to provide a white solid m.p. 120–122°.

Analysis: Calc. for $C_{26}H_{33}NO_3$ 76.62 % C, 8.16 % H, 3.44 % N. Found: 76.44 % C, 8.18 % H, 3.31 % N.

EXAMPLE 20A

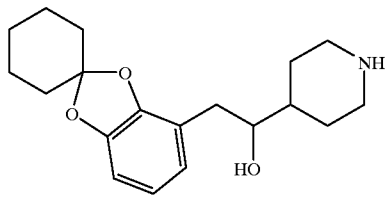

Intermediate: 2-(4-Piperidinyl-1H)-1-spiro(1,3-benzodioxole-2,1'-cyclohexane)-2-ethanol A mixture of 2-(1-benzyl-4-piperidinyl)-1-spiro(1,3-benzodioxole-2,1'-cyclohexane)-2-ethanol (3.4 g, 8.3 mmol), 10% Pd/C (0.5 g), cyclohexene (13.8 g, 168.0 mmol) and methanol (72 ml) was stirred at reflux under $N_2$ for 4 hours. The cooled reaction was filtered through a bed of celite and the filtrate was concentrated to yield a white solid, which was recrystallized from ethyl acetate to yield a white solid mp 145–147° C.

Analysis: Calc. for $C_{19}H_{27}N_1O_3$ 71.89 % C, 8.57 % H, 4.41 % N. Found: 71.68 % C, 8.67 % H, 4.34 % N.

EXAMPLE 20B

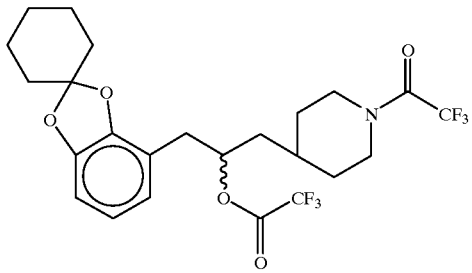

A mixture of 2-(4-piperidinyl-1H)-1-spiro(1,3-benzodioxole-2,1'-cyclohexane)-2-ethanol (141.7 g, 0.45 mol), anhydrous $CH_2Cl_2$ and triethylamine (127.1 g, 1.26 mol) are stirred under $N_2$. The solution is cooled in ice-salt over 2 hours to about −2° C. Trifluoroacetic anhydride (234.9 g to 1.12 mol) is added dropwise over 4.5 hours and the solution is stirred at ambient temperature for 17 hours. The reaction is concentrated to 500 g and diluted with 600 ml water and extracted with $CH_2Cl_2$ (400 ml). The extract is washed with water, dried with $K_2CO_3$ and concentrated.

EXAMPLE 20C

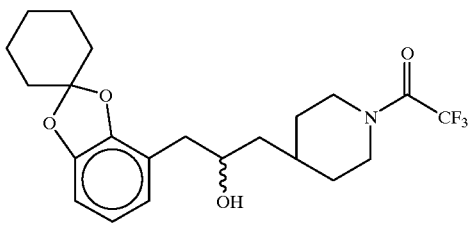

The compound of example 20B is dissolved in 3.75 l MeOH and stirred under $N_2$ at ambient temperature for 2 hours. The reaction is filtered and the concentrate is diluted with water (250 ml) and extracted with $Et_2O$. The aqueous phase is saturated with NaCl and extracted further with $Et_2O$ (300 ml) (3×300 ml). The extract was washed with brine, dried with $MgSO_4$ and concentrated.

EXAMPLE 21

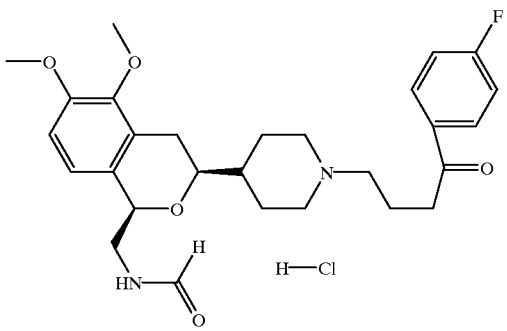

When formula I is $R_1=(CH_2)_3C(=O)$ phenyl substituted with fluoro; $R_2=H$, $R_3=$formyl; X and Y=methoxy.

N-[3-[1-[4-(4-Fluorophenyl)-4-oxobutyl]-4-piperidinyl]-3,4-dihydro-5,6-dimethoxy-1H-2-benzopyran-1-ylmethyl] formamide Hydrochloride A mixture of N-(3,4-dihydro-5,6-dimethoxy-3-(4-piperidinyl)-1H-2-benzofuran-1-ylmethyl]formamide (4.0 g, 12 mmol) 4-chloro-1-4'-fluorobutyrophenone-4-fluorophenylbutyrophenone (3.6 g, 18.0 mmol), $K_2CO_3$ (2.5 g), KI (60 mg) and toluene (150 ml) was stirred and refluxed for 48 h. The reaction was filtered and the filtrate was concentrated to 8.2 g of a yellow oil. The oil was chromatographed on the HPLC on silica gel, eluting with 10% MeOH/$CH_2Cl_2$. Concentration of the appropriate fractions gave a glassy oil which was dissolved in EtOH and ethereal HCl added to precipitate a white hydrochloride salt, mp 168–170° C.

Analysis: Calculated for $C_{28}H_{36}ClFN_2O_5$: 62.85% C, 6.78% H, 5.24% N. Found: 62.77% C, 6.79% H, 4.98% N.

EXAMPLE 22

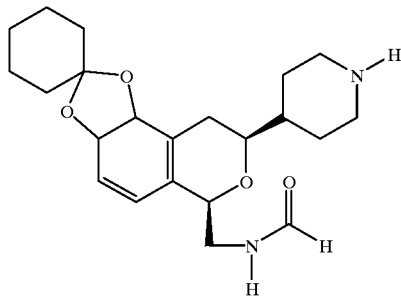

When Formula I is $R_1$=H; $R_2$=H; $R_3$=(C=O)H; X and Y form cyclohexylideneketal
cis-N-[5,6-Cyclohexylidenedioxy]-3,4-dihydro-3-(4-piperidinyl)-1H-2-benzopyran-1-ylmethyl) formamide A solution of N-[cis-5,6-(cyclohexylidenedioxy)-3,4-dihydro-3-(1-trifluoroacetyl-4-piperidinyl)-1H-2-benzopyran-1-ylmethyl]formamide (39.1 g, 0.081 mol) and 50% EtOH-THF (390 ml) was stirred at ambient temperature under nitrogen and $NaBH_4$ (3.15 g, 0.083 mol) was added. The reaction was stirred at ambient temperature for 1 hour and was concentrated to yield a white solid. The product was triturated with $H_2O$, filtered and dried to afford a white solid. Flash chromatography over silica gel using 10% $NH_4OH$—MeOH provided pure material which was recrystallized twice from toluene to give a white powder, mp 205–207°.

Analysis: Calc. for $C_{22}H_{30}N_2O_4$ 68.37 % C, 7.82 % H, 7.25 % N. Found: 68.64 % C, 7.69 % H, 7.01 % N.

EXAMPLE 23

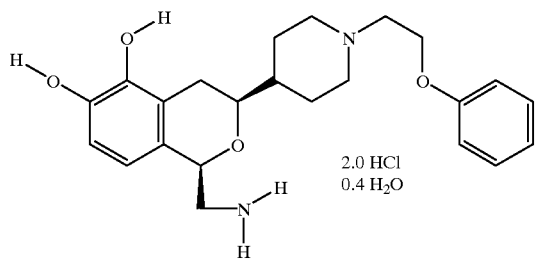

2.0 HCl
0.4 $H_2O$

When Formula I is $R_1$=$(CH_2)_mZ(CH_2)_2$phenyl; Z=O; n=1; $R_2$ and $R_3$=H; X and Y=OH.
cis-1-(Aminomethyl)-3,4-dihydro-3-[1(2-phenoxyethyl)-4-piperidinyl]-1H-2-benzopyran-5,6-diol dihydrochloride 0.4 hydrate A solution of cis-1-(aminomethyl)-5,6-(cyclohexylidenedioxy)-3,4-dihydro-3-[1-(2-phenoxyethyl)-4-piperidinyl]-1H-2-benzopyran (1.1 g, 2.3 mmol) and a 5M solution of concentrated HCl in ethanol (20 ml) was stirred at reflux under $N_2$ for 1 hour and a white solid precipitated. The reaction was cooled in an ice bath and the resultant product was collected. The compound was recrystallized from methanol-ether and dried at 80 for 4 hours to afford a white solid, mp 288–290°.

Analysis: Calc. for $C_{23}H_{32}Cl_2N_2O_4$.0.4 $H_2O$ 57.71 % C, 6.92 % H, 5.85 % N. Found: 57.57 % C, 6.97 % H, 5.80 % N.

EXAMPLE 24

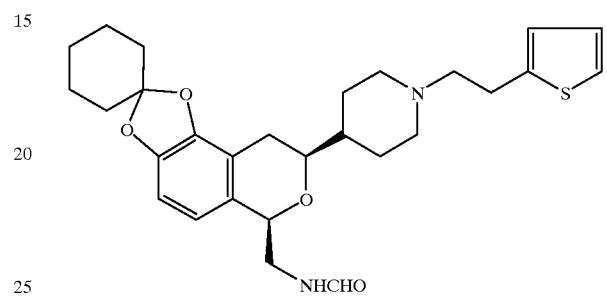

Wherein Formula I where $R_1$ is heteroarylalkyl, $R_2$ is H, $R_3$ is formyl, X and Y form cyclohexylideneketal.
cis-N-[5,6-(cyclohexylidinedioxy)-3,4-dihydro-3-[1(2-(thiophen-2-yl)ethyl)-4-piperidinyl]-1H-2-benzofuran-1-ylmethyl]formamide A mixture of cis-[N-5,6-cyclohexylidenedioxy)-3,4-dihydro-3-(4-piperidinyl-1H-2-benzopyran-1-ylmethyl) formamide (5.0 g, 12.9 mmol), methanesulfonic acid 2-thiophen-2-yl ethyl ester (2.9 g, 14.0 mmol), $NaHCO_3$ (1.2 g) and DMF (100 ml) was stirred at 65° C. for 5 h. The reaction was poured into $H_2O$ and after extractive workup with EtOAc there remained an oil, which solidified to a white solid. Recrystallization yielded the product, while an analytical sample was obtained by recrystallization from EtOAc-heptane to afford the formamide as a white solid, mp 142–144° C.

Analysis: Calc. for $C_{28}H_{36}N_2O_4S$: 67.71 % C, 7.31 % H, 5.64 % N. Found: 67.65 % C, 7.47 % H, 5.60 % N.

EXAMPLE 25

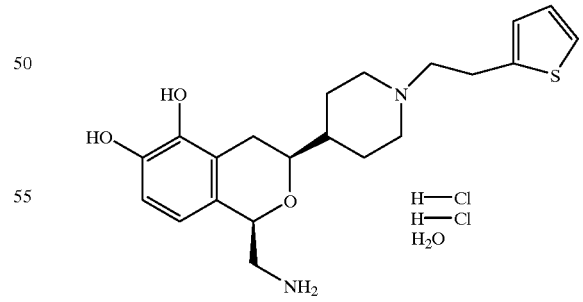

H—Cl
H—Cl
$H_2O$

When Formula I is $R_1$=heteroarylalkyl; $R_2$ and $R_3$=H; X and Y=OH.
cis-1-Aminomethyl-3,4-dihydro-3-[1-(2-(thiophen-2-yl) ethyl-4-piperidinyl]-1H-2-benzopyral-5,6-diol Dihydrochloride Hydrate A solution of cis-N-[5,6-(cyclohexylidenedioxy)-3-[1-(2-thiophen-2-yl)ethyl)piperidi-4-yl]-3,4-dihydro-1H-2- benzofuran-1-yl]methylformamide (1.4 g, 3.0 mmol) and 5M of concentrated Hcl in EtOH (20 ml) was refluxed for 2 h. The reaction was stored at 10° C. for 16 h, and a solid was collected. This sample was combined with a 0.2 g sample from a previous run and the combined sample recrystallized from EtOH to yield a white solid, mp 185–187° C.

Analysis: Calc. for $C_{21}H_{28}N_2O_4 \cdot 2HCl \cdot H_2O$: 52.61 % C, 6.73 % H, 5.84 % N. Found: 52.69 % C, 6.76 % H, 5.55 % N.

EXAMPLE 26

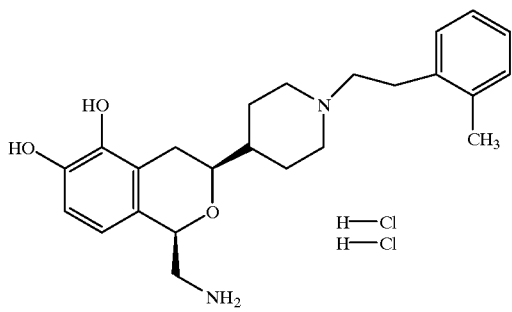

When Formula I is $R_1$=arylalkyl substituted with methyl; $R_2$ and $R_3$=H; X and Y=OH.

cis-1-Aminomethyl-3,4-dihydro-3-[1-[2-(2-methylphenyl)ethyl]-4-piperidinyl]-1H-2-benzopyran-5,6-diol Dihydrochloride A solution of cis-1-(aminomethyl)-5,6-(cyclohexylidenedioxy-3,4-dihydro-3-[1-[2-(2-methylphenyl)ethyl-4-piperidinyl]-1H-2-benzopyran (1.2 g, 2.5 mmol) and 5 M of concentrated HCl in EtOH (15 ml) was refluxed for 2 h. As the reaction was proceeding, a white solid separated from solution. The reaction was allowed to stand at ambient temperature for 2 h, and the white solid was collected. The solid was dried at 80° C. under vacuum for 4 h to afford the product as a white dihydrochloride salt, mp 312–314° C.

Analysis: Calc. for $C_{24}H_{32}N_2O_3 \cdot 2HCl$ 61.40 % C, 7.30 % H, 5.97 % N. Found: 61.00 % C, 7.48 % H, 5.82 % N.

EXAMPLE 27

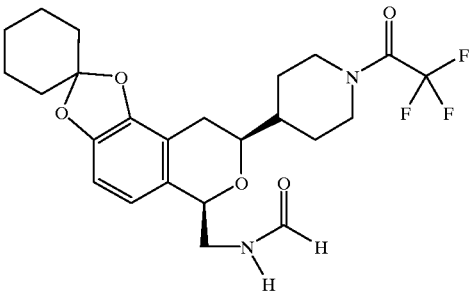

When Formula I is $R_1$=trifluoroacetyl; $R_2$=H; $R_3$=(C=O)H; X and Y form cyclohexylidene ketal.

cis-N-[5,6-(Cyclohexylidenedioxy)-3,4-dihydro-3-(1-trifluoroacetyl-4-piperidinyl)-1H-2-benzopyran-1-ylmethyl]formamide A solution of 4-[1-hydroxyethyl-2-spiro(1,3-benzodioxole-2,1'-cyclohexane)]-1-piperidine (21.0 g, 0.051 mol) formylaminoacetaldehyde dimethylacetal (8.1 g, 0.061 mol) and anhydrous $CH_2Cl_2$ (200 ml) was stirred under $N_2$ and cooled to −3°. $BF_3 \cdot OEt_2$ (37.6 ml, 0.306 mol) was added dropwise over 45 minutes maintaining the temperature at −3°. After complete addition, the reaction was stirred at −3° for 30 minutes and then at ambient temperature for 19 hours. Saturated $Na_2CO_3$ was added dropwise until foaming ceased. The organic phase was washed with saturated $Na_2CO_3$, washed with water, dried with $K_2CO_3$ and concentrated to yield 22.9 g of a dark oil. The oil was triturated with $Et_2O$ to produce a solid that was collected to yield a white solid. The filtrate was concentrated to yield a beige foam. The two samples were combined and chromatographed over 1.0 kg silica gel eluting with EtOAc to afford a white solid. A 400 mg sample was recrystallized from IPA-$H_2O$ to provide 270 mg of a fluffy white solid, mp 72–174° C.

Analysis: Calc. for $C_{24}H_{29}F_3N_2O_5$: 59.74 % C, 6.06 % H, 5.81 % N. Found: 59.52 % C, 6.04 % H, 5.80 % N.

EXAMPLE 28

Formula I wherein $R_1$ is diphenyl $C_{1-6}$alkyl substituted with F; X and Y form cyclohexylideneketal; $R_2$ is hydrogen, $R_3$ is formyl.

cis-N-[3-[1-[4,4-Bis-(4-fluorophenyl)butyl]-4-piperidinyl]-5,6-(cyclohexylidenedioxy)-3,4-dihydro-1H-2-benzopyran-1-ylmethyl]formamide Oxalate Hemihydrate A mixture of N-[5,6-(cyclohexylidenedioxy)-3-(piperidin-4-yl)-3,4-dihydro-1H-2-benzopyran]formamide (2.3 g, 5.9 mmol), methanesulfonic acid 4,4-bis-(4-fluorophenyl)butyl ester (2.2 g, 6.5 mmol), $NaHCO_3$ (1.0 g, 11.8 mmol) in DMF (50 ml) was stirred and heated under $N_2$ for 2 h at 65° C. The reaction was stirred at ambient temperature for 16 h, and then it was poured into $H_2O$. After extractive workup with EtOAc, there remained 3.5 g of a brown oil. This oil was combined with a sample from another run and the combined sample was flash chromatographed on silica (200 g), eluting with $CH_2Cl_2$—MeOH (4%). The desired fractions were combined and concentrated to afford a white amorphous solid. The solid was dissolved in $Et_2O$ and oxalic acid (0.58 g, 6.4 mmol) was added. The reaction was warmed briefly on the steam bath and a white oxalate salt was collected. The salt was recrystallized from IPA-$Et_2O$ to afford the oxalate salt of the product as white solid, mp 148–150° C.

Analysis: Calc. for $C_{39}H_{44}F_2N_2O_4.C_2H_2O_4.0.5$ $H_2O$: 65.82% C, 6.49% H, 3.83% N. Found: 65.92% C, 6.42% H, 3.73% N.

EXAMPLE 29

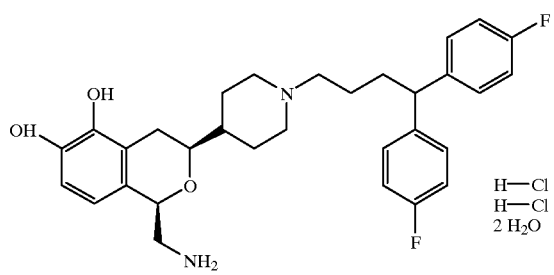

When Formula I is $R_1$=diphenyl $C_{1-6}$alkyl substituted with F; $R_2$ and $R_3$=H, X and Y=OH.

cis-1-(Aminomethyl)3-[1-[4,4-bis-(4-fluorophenyl)butyl]-4-piperidinyl]-1H-2-benzopyran-5,6-diol Dihydrochloride Dihydrate A solution of cis-1-(aminomethyl)-5,6-(cyclohexylidenedioxy)-3-[1-[4,4-bis(4-fluorophenyl)butyl]-4-piperidinyl]-1H-2-benzopyran (1.0 g, 1.6 mmol) and 5M HCl in EtOH (20 ml) was refluxed for 1 h. The reaction was concentrated to a brown oil, and the oil dissolved in absolute EtOH. Ether was then added to precipitate 0.8 g of a white solid. The product was combined with a 0.2 g sample from another run, and the combined sample recrystallized from EtOH-$Et_2O$ and then from EtOH to afford an off-white solid. The compound was dried at 80° C. under vacuum to yield the salt as a dihydrochloride, dihydrate, mp, 185–187° C.

Analysis: Calc. for $C_{31}H_{36}F_2N_2O_3.2HCl.2H_2O$: 58.95 % C, 6.70 % H, 4.44 % N. Found: 59.02 % C, 6.69 % H, 4.43 % N.

EXAMPLE 30

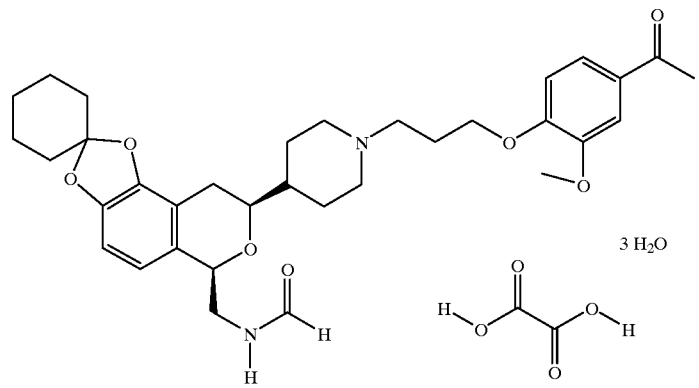

Wherein Formula I is $R_1$=$(CH_2)_mZ(CH_2)_t$ substituted phenyl; X and Y form cyclohexylidenedioxy; $R_2$=H and $R_3$=CHO.

cis-N-[3-[1-[3-(4-acetyl-2-methoxyphenoxy)propyl]-4-piperidinyl]-5,6-(cyclohexylidenedioxy)-3,4-dihydro-1H-2-benzopyran-1-ylmethyl]formamide oxalate Trihydrate 1-[4-(3-Chloropropoxy)-3-methoxyphenyl]ethanone (0.14 g, 0.00057 mol), potassium carbonate (0.08 g, 0.00057 mol), and potassium iodide (0.02 g, 0.00010 mole) were added sequentially to a stirred solution of cis-N-[5,6-cyclohexylidenedioxy)-3,4-dihydro-4-piperidinyl-1H-2-benzopyran-3-ylmethyl]formamide (0.200 g, 0.00052 mole) in N,N-dimethylformamide (10 ml) at room temperature. After stirring overnight at 65° C., the mixture was diluted with water and extracted into ethyl acetate. Purification via chromatotron (2 mm silica gel plate) eluting with 5% MeOH/DCM gave 0.250 g of a white foam. Formation of the oxalate salt followed by recrystallization from MeOH/ether yielded a white solid, mp 100–103° C.

Analysis: Calc. for $C_{36}H_{46}N_2O_{11}.3H_2O$: 58.68 % C, 7.11 % H, 3.80 % N. Found: 58.19 % C, 6.27 % H, 3.59 % N.

EXAMPLE 31

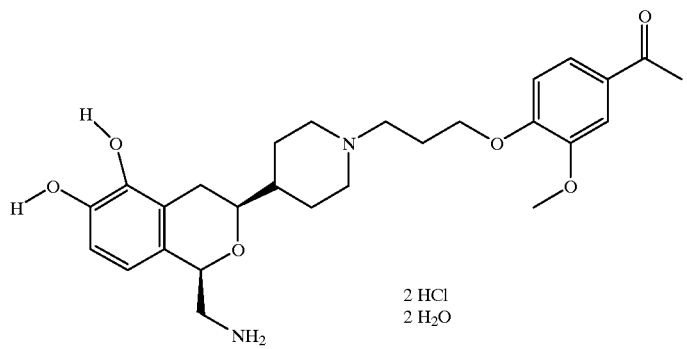

Wherein Formula I is $R_1=(CH_2)_mZ(CH_2)_t$ substituted phenyl; X and Y=OH; $R_2R_3$=H.

cis-1-(3-[3-[4-[1-(Aminomethyl)-3,4-dihydro-5,6-dihydroxy-1H-2-benzopyran-3-yl]-1-piperidinyl]propoxy]-3-methoxyphenyl)ethanone Dihydrochloride Dihydrate cis-1-[3-[3-[4-[1-(Aminomethyl)-5,6-(cyclohexyldenedioxy)-3,4-dihydro-1H-2-benzopyran-3-yl]-1-piperidinyl]propoxy]-3-methoxyphenyl]ethanone (1.0 g, 0.0018 mole) was added to a 5M solution of concentrated HCl in ethanol (20 ml). After heating under reflux for 3 h, the solvent was concentrated in vacuo to a brown foam. The addition of ethanol solidified the material. Trituration of the solid with hot ethanol yielded an off-white solid, mp 218–220° C.

Analysis: Calc. for $C_{27}H_{38}Cl_2N_2O_6.2H_2O$: 54.64 % C, 7.13 % H, 4.72 % N. Found: 54.94 % C, 6.87 % H, 4.63 % N.

EXAMPLE 32

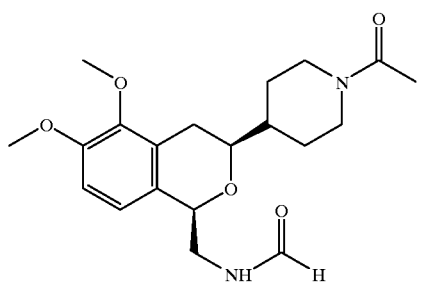

When Formula I is $R_1$=C(O)CH$_3$; $R_2$=H; $R_3$=CHO; X and Y=methoxy.

Cis-N-[3-(1-Acetyl-4-piperidinyl)-3,4-dihydro-5,6-dimethoxy-H-2-benzopyran-1-ylmethyl]formamide A solution of 4-(2-(2,3-dimethoxyphenyl)-1-hydroxyethyl)piperidine (3.8 g, 0.014 mol) in acetic anhydride (20 ml) was heated between 60–65° C. for 5 minutes. After cooling to ambient temperature, the reaction was diluted with water, cooled in an ice bath and 50% aqueous NaOH was added until the reaction was basic. Extractive workup with EtOAc yielded an oil, which upon purification on the preparative HPLC (3% MeOH/CH$_2$Cl$_2$) afforded 2.7 g of 4-(2,3-dimethoxyphenyl-1-hydroxyethyl)piperidine-1-acetamide as a colorless oil.

To a stirred solution of 4-(2,3-dimethoxyphenyl-1-hydroxyethyl)piperidine-1-acetamide (2.4 g, 0.0078 mol), N-formylaminoacetaldehyde dimethylacetal (1.2 g, 0.0093 mol) in CH$_2$Cl$_2$ (40 ml), cooled to 5° C., was added dropwise BF$_3$.O(Et)$_2$ (7.9 g, 0.047 mol). After complete addition, the cooling bath was removed and the reaction was allowed to proceed at room temperature for 2 h, at which time an additional 2.0 equiv. of BF$_3$.O(Et)$_2$ was added. The reaction was allowed to stand at ambient temperature for 64 h, and then it was poured into water. The organic layer was collected, washed with saturated Na$_2$CO$_3$ and brine, dried (K$_2$CO$_3$) and concentrated to yield an oil, which upon trituration with ether yielded a white solid. This solid was combined with another and the combined sample was recrystallized from toluene (twice) to yield the compound as a white solid, mp 140–142° C.

Analysis: Calculated for $C_{20}H_{28}N_2O_5$: 63.81% C, 7.50% H, 7.44% N. Found: 63.68% C, 7.46% H, 7.24% N.

EXAMPLE 33

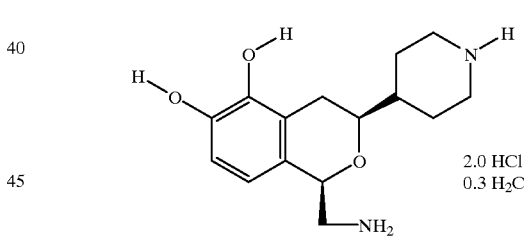

When Formula I is $R_1$=H; $R_2$ and $R_3$=H; X and Y=OH.

cis-1-(Aminomethyl)-3,4-dihydro-3-(4-piperidinyl)-1H-2-benzopyran-5,6-diol Dihydrochloride 0.3 Hydrate A solution of cis-N-[5,6-(cyclohexylidenedioxy)-3,4-dihydro-3-(4-piperidinyl)-1H-2-benzopyran-1-ylmethyl]-formamide (0.70 g, 1.8 mmol) and 5M Hcl in ethanol (15 ml) was stirred at reflux under N$_2$ for 1 hour and a white solid precipitated. The reaction was cooled in an ice bath and the resultant product was collected to yield the titled compound which was recrystallized from methanol-ether and dried at 80° C. for 4 hours to afford a white solid mp 305–307° C.

Analysis: Calc. for $C_{15}H_{24}Cl_2N_2O_3.0.3$ H$_2$O 50.50 % C, 6.97 % H, 7.86 % N. Found: 50.65 % C, 6.93 % H, 7.81 % N.

EXAMPLE 34

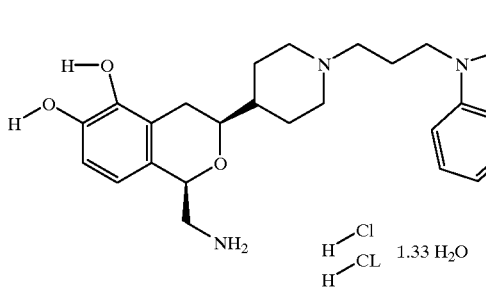

Formula I wherein X and Y=OH, R₁=heteroarylalkyl, R₂ and R₃=H.
cis-1-[3-[4-(1-Aminomethyl-3,4-dihydro-5,6-dihydroxy-1H-2-benzopyran-3-yl)-1-piperidinyl]propyl]-1,3-dihydrobenzimidazol-2-one Dihydrochloride 1.33 Hydrate Cis-N-[5,6-(Cyclohexylidene)-3,4-dihydro-3-[1-[3-(2-oxo-2,3-dihydro-benzimidazol-1-yl)propyl]-4-piperidinyl]-1H-2-benzopyran-1-ylmethyl]formamide (0.750 g, 0.0013 mole) was added to a 5M solution of concentrated HCl in ethanol (15 ml) at room temperature. After heating under reflux for 1 h, a white solid precipitated out of solution. After cooling to room temperature, the solid was collected by filtration and dried at 80° C. for 5 h to yield a solid; mp 219–221° C.

Analysis: Calc. for $C_{25}H_{34}Cl_2N_4O_4 \cdot 1.33\ H_2O$: 54.65 % C, 6.73 % H, 10.20 % N. Found: 54.29 % C, 6.69 % H, 10.06 % N.

EXAMPLE 35

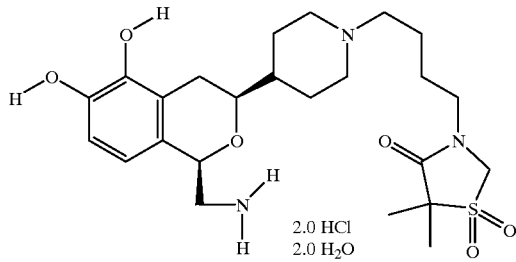

Formula I where X and Y=OH, R₁=heteroarylalkyl, R₂ and R₃=H
3-[4-[4-(cis-1-(Aminomethyl)-3,4-dihydro-5,6-dihydroxy-1H-2-benzopyran-3-yl)-piperidin-1-yl]butyl]-5,5-dimethyl-1,1-dioxo-4-thiazolidinone Dihydrochloride Dihydrate A solution of 3-[4-[4-(cis-5,6-(cyclohexylidenedioxy)-3,4-dihydro-1-(N-formylaminomethyl)-1H-2-benzopyran-3-yl)piperidin-1-yl]butyl]-5,5-dimethyl-1,1-dioxo-4-thiazolidinone (1.0 g, 1.7 mmol) and 5M HCl in ethanol (15 ml) was stirred at reflux under N₂ for 3.5 hours. The cooled reaction was concentrated to yield 1.2 g of a beige oil. The residue was triturated with ether and the solvent was evaporated to give a tacky solid. The product was crystallized from boiling methanol to afford a white solid. The compound was dried at 80° C. for 4 hours to afford a white solid mp 211–214° C.

Analysis: Calc. for $C_{24}H_{39}Cl_2N_3O_6S \cdot 2.0\ H_2O$: 47.68% C, 7.17% H, 6.95% N. Found: 47.38% C, 7.15% H, 6.90% N.

EXAMPLE 36

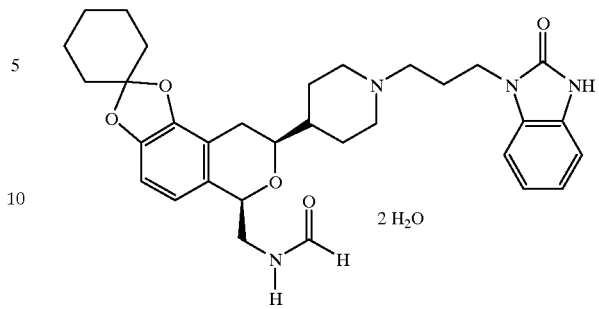

Formula I wherein X and Y form cyclohexylidenedioxy, R₁=heteroarylalkyl, R₂=H, R₃=CHO
cis-N-[5,6-(Cyclohexylidenedioxy)-3,4-dihydro-3-[1-[3-(2-oxo-2,3-dihydrobenzimidazole-1-yl)propyl]-4-piperidinyl]-1H-2-benzopyran-1-ylmethyl)]formamide dihydrate 1-(3-Chloropropyl)-1,3-dihydrobenzimidazol-2-one (3.0 g, 0.0142 mol), potassium carbonate (1.97 g, 0.0142 mol), and potassium iodide (0.43 g, 0.0026 mol) were added sequentially to a stirred solution of cis-N-[5,6-(cyclohexylidenedioxy)-3,4-dihydro-4-piperidinyl-1H-2-benzopyran-3-ylmethyl]formamide (5.0 g, 0.0129 mol) in N,N-dimethylformamide (250 ml) at room temperature. After stirring overnight at 65° C., the mixture was diluted with water and extracted into ethyl acetate. Purification via flash column chromatography eluting with 5% MeOH/DCM gave 2.53 g (35%) of a pale yellow foam. Further purification of 1.0 g of this material via chromatotron (6 mm silica gel plate) eluting with 5% MeOH/DCM gave 0.640 g of a white foam. Addition of methanol solidified the material to a white solid. Recrystallization from methanol yielded a white solid. The solid was collected by filtration and dried overnight at 100° C. to yield a white solid, mp 145–147C.°.

Analysis: Calc. for $C_{32}H_{40}N_4O_5 \cdot 2H_2O$: 64.41 % C, 7.43 % H, 9.39 % N. Found: 64.17 % C, 6.94 % H, 9.36% N

EXAMPLE 37

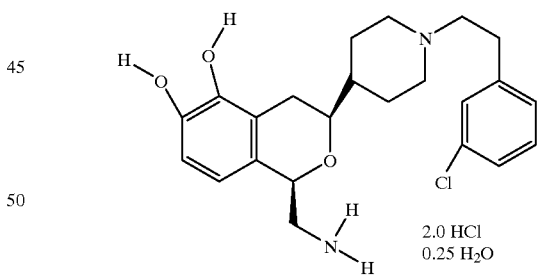

Formula I wherein R₁ is substituted aralkyl, R₂ and R₃=H, X and Y=OH
cis-1-(Aminomethyl)-3,4-dihydro-3-[1-[2-(3-chlorophenyl)]-4-piperidinyl]-1H-2-benzopyran-5,6-diol Dihydrochloride 0.25 Hydrate A solution of cis-N-[5,6-(cyclohexylidenedioxy)-3,4-dihydro-3-[1-(3-chlorophenethyl)-4-piperidinyl]-1H-2-benzopyran-1-ylmethyl]formamide (900 mg, 1.7 mmol) and 5M solution of concentrated HCl in ethanol (12 ml) was stirred at reflux under N₂ for 1 hour and a white solid precipitated. The reaction was cooled in an ice bath and the resultant product was collected. The compound was dried at 80° for 4 hours to afford a white solid mp 313–316° C.

Analysis: Calc. for $C_{23}H_{31}Cl_3N_2O_3 \cdot 0.25\ H_2O$: 55.87% C, 6.44% H, 5.67% N. Found: 55.90% C, 6.17% H, 5.62% N.

EXAMPLE 38

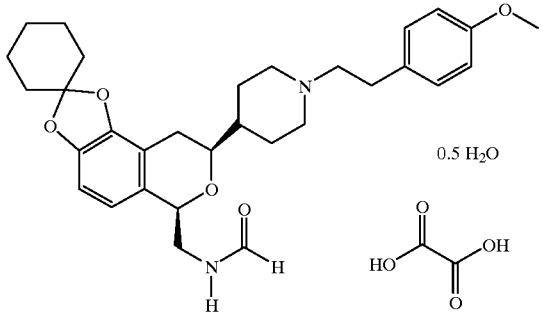

0.5 H$_2$O

Formula I wherein $R_1$=substituted arylalkyl, $R_2$=H, $R_3$=CHO, X and Y form cyclohexylidenedioxy.
cis-N-[5,6-(Cyclohexylidenedioxy)-3,4-dihydro-3-[1-[2-(4-methoxyphenyl)ethyl]-4-piperidinyl]-1H-2-benzopyran-1-ylmethyl]formamide Oxalate Hemihydrate Methanesulfonic acid-2-(4-methoxyphenyl)ethyl ester (3.28 g, 0.0142 mol) and potassium carbonate (1.97 g, 0.0142 mol) were added sequentially to a stirred solution of cis-N-[5,6-(cyclohexylidenedioxy)-3,4-dihydro-4-piperidinyl-1H-2-benzopyran-3-ylmethyl]formamide (5.0 g, 0.0129 mol) in N,N-dimethylformamide (250 ml) at room temperature. After stirring overnight at 65° C., the mixture was diluted with water and extracted into ethyl acetate. Purification via flash column chromatography eluting with 5% MeOH/DCM gave a yellow foam. Further purification of 0.800 g of this material via chromatotron (4 mm silica gel plate) eluting with 5% MeOH/DCM gave a white foam. Formation of the oxalate salt followed by recrystallization from methanol yielded a white solid mp 131–133° C.

Analysis: Calc. for $C_{33}H_{42}N_2O_9 \cdot 0.5H_2O$: 63.96 % C, 6.99 % H, 4.52 % N. Found 64.18 % C, 6.99 % H, 4.45 % N.

EXAMPLE 39

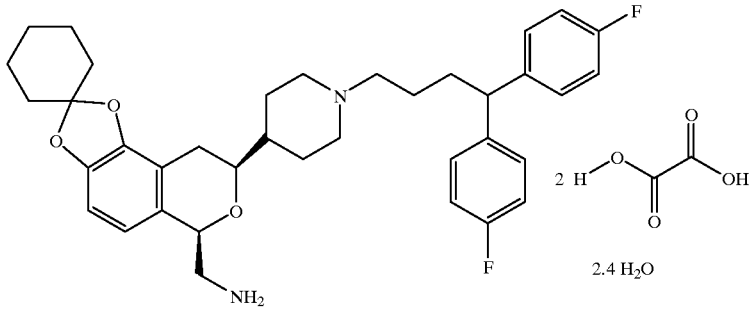

2.4 H$_2$O

Formula I where $R_1$=substituted arylalkyl, $R_2$ and $R_3$=H, X and Y form cyclohexylidenedioxy
cis-1-Aminomethyl-5,6-(cyclohexylidenedioxy)-3,4-dihydro-3-[1-[4,4-bis(4-fluorophenyl)butyl]-4-piperidinyl]-1H-2-benzopyran Dioxalate 2.4 Hydrate A solution of the formamide of example 28 (0.5 g, 0.8 mmol) in THF-MeOH (5 ml-5 ml) and 15% NaOH (2.5 ml) was stirred at 50° C. for 4 h. Most of the solvent was removed in vacuo, and the residue was diluted with H$_2$O and a yellow gum resulted. The aqueous suspension was extracted with EtOAc, and the extract was washed (H$_2$O), dried (MgSO$_4$) and was concentrated yielding 0.6 g of a tacky solid. The solid was flash chromatographed on silica gel eluting with a gradient of MeOH in CH$_2$Cl$_2$ (5, 8 & 10%). Concentration of the appropriate fractions gave 0.4 g of a yellow foam. The foam was dissolved in Et$_2$O and oxalic acid (0.13 g, 1.4 mmol) was added to afford an off-white oxalate salt. The salt was recrystallized from EtOH to yield the compound as a white solid, mp 153–155° C.

Analysis: Calc. for $C_{37}H_{44}F_2N_2O_3 \cdot 2C_2H_2O_4$ 2.4 H$_2$O 59.54 % C, 6.39 % H, 3.37 % N. Found: 59.80 % C, 5.97% H, 3.29 % N.

EXAMPLE 40

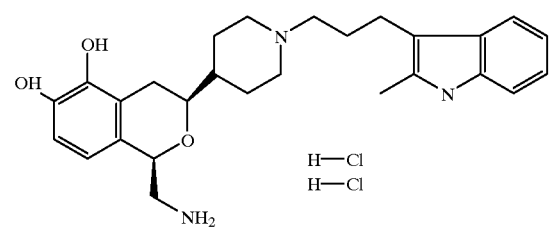

Formula I wherein $R_1$ is substituted arylalkyl, X and Y=OH, $R_2$ and $R_3$=H.

cis-1-(Aminomethyl)-3,4-dihydro-3-[1-[3-(2-methyl-1H-indol-3-yl)propyl]-4-piperidinyl]-1H-2-benzopyran-5,6-diol Dihydrochloride Cis-N-[5,6-[cyclohexylidenedioxy)-3,4-dihydro-3-[1-[3-(2-methyl-1H-indol-3-yl)propyl]-4-piperidinyl]-1H-2-benzopyran-1-ylmethyl]formamide (0.750 g, 0.0013 mole) was added to a 5M solution of concentrated HCl in ethanol (15 ml) at room temperature. After stirring under reflux for 1 h, a blue solid precipitated out of solution. The solid was collected by filtration and dried at 80° C. for 5 h to yield a gray solid, mp 265–267° C.

Analysis: Calc. for $C_{27}H_{37}Cl_2N_3O_3$: 62.06 % C, 7.14 % H, 8.04 % N. Found: 61.98 % C, 7.42 % H, 7.49 % N.

EXAMPLE 41

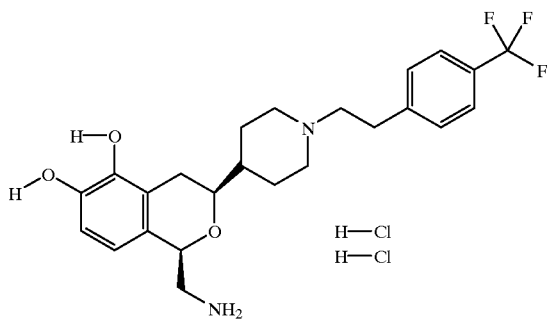

Formula I wherein $R_1$=substituted arylalkyl, X and Y=OH, $R_2$ and $R_3$=H.
cis-1-(Aminomethyl)-3,4-dihydro-3-[1-[2-(4-trifluoromethylphenyl)ethyl]-4-piperidinyl]-1H-2-benzopyran-5,6-diol Dihydrochloride Cis-N-[5,6-(cyclohexylidenedioxy)-3,4-dihydro-3-[1-[2-(4-trifluoromethylphenyl)ethyl]-4-piperidinyl]-1H-2-benzopyran-1-ylmethyl]formamide (0.500 g, 0.00089 mol) was added to a 5M solution of concentrated HCl in ethanol (10 ml) at room temperature. After stiring under reflux for 1 h, a white solid precipitated out of solution. The solid was collected by filtration and dried at 80° C. for 5h to yield a solid, mp 299–300° C.

Analysis: Calc. for $C_{24}H_{31}Cl_2F_3N_2O_3$: 55.07 % C, 5.97 % H, 5.35 % N. Found: 54.88 % C, 6.21 % H, 5.29 % N.

EXAMPLE 42

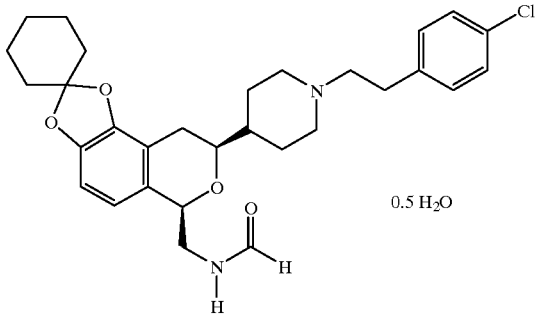

Formula I wherein $R_1$=substituted arylalkyl, $R_2$=H, $R_3$=CHO, X and Y form a cyclohexylidenedioxy
cis-N-[3-[1-[2-(4-Chlorophenyl)ethyl]-4-piperidinyl]-5,6-(cyclohexylidenedioxy)-3,4-dihydro-1H-2-benzopyran-1-ylmethyl]formamide Hemihydrate Methanesulfonic acid-2-(4-chlorophenyl)ethyl ester (3.34 g, 0.0142 mol) and potassium carbonate (1.97 g, 0.0142 mol) were added sequentially to a stirred solution of cis-N-[5,6-(cyclohexylidenedioxy)-3,4-dihydro-4-piperidinyl-1H-2-benzopyran-3-ylmethyl]formamide (5.0 g, 0.0129 mol) in N,N-dimethylformamide (250 ml) at room temperature. After stirring overnight at 65° C., the mixture was diluted with water and extracted into ethyl acetate. Purification via flash column chromatography eluting with 5% MeOH/DCM gave 3.14 g (46%) of a white foam. Further purification of 0.880 g of this material via chromatotron (4 mm silica gel plate) eluting with 5% MeOH/DCM gave a colorless oil. The addition of methanol solidified the material to a white solid. Recrystallization twice from methanol yielded a white solid mp 90–92° C.

Analysis: Calc. for $C_{30}H_{37}ClN_2O_4 \cdot 0.5\ H_2O$: 67.47 % C, 7.17 % H, 5.24 % N. Found: 67.52 % C, 7.43 % H, 5.27 % N.

A therapeutically effective amount of the compounds of the present invention is administered to a patient in need of such therapy, that is a patient suffering from psychosis. Preferably, compounds of the present invention are administered between 0.01 milligram per killogram per day (mg/kg/day) to 100 mg/kg/day. However, relevant factors such as species of mammal, size, age, general health of the patient, severity of the disease, idiosyncratic responses of the patient, route of administration and the like may vary the dosage required.

Likewise the route of administration may be varied depending upon a variety of the foregoing factors and also including the biopharmaceutical characteristics of the compound as may be ascertained by one skilled in the art. Examples of preferred routes of administration include oral, buccal, sublingual, intravenous, intraperineal, inhalation, subcutaneously, rectally, topically and transdermally. See for example, Remington's Pharmaceutical Sciences, 18th edition, Mack Publishing Co. (1990), incorporated herein by reference.

The compounds of the present invention can be administered alone or in the form of a pharmaceutically acceptable composition which includes pharmaceutically acceptable carriers, the proportion and nature of which are determined by the characteristics of the compound of the present invention, the route of administration and standard pharmaceutical practice. The compounds may be in the form of their pharmaceutically acceptable salt forms such as acid addition salts or base addition salts thereof.

The compounds of the present invention antagonize the effects of dopamine at the $D_2$-type dopamine receptor as may be shown by standard binding data or the following in vivo test.

HUMAN DOPAMINE $D_{2L}$ ASSAY RECEPTOR BINDING

The affinity of a compound for the dopamine $D_2$ receptor is proportional to its antipsychotic potency (Creese et al., 1978). The dopamine $D_2$ receptor gene was isolated from a human striatal (caudate/putamen) cDNA library; the long splice variant (Dal Toso et al., 1989), $D_{2L}$ was sequenced and subcloned into an expression vector and stably transfected in Chinese Hamster Ovary cells. A single high expressing clonal cell line was isolated and membranes from this cell line were used for receptor binding assays. The ability of compounds to displace the binding of [$^3$H]N-methyl spiroperidol (0.4 nM) to the $D_{2L}$ receptor was measured (Hall et al., 1990). The incubation buffer contained: 50 mM Tris, 120 mM NaCl; 5 mM Kcl; 2 mM $CaCl_2$; 1 mM $MgCl_2$; pH 7.7). For most assays, a 1 mM stock solution of test compound in water was prepared and diluted in incubation buffer to obtain concentrations in a range appropriate for determining the $IC_{50}$ for the compound. Incubations were performed at 37° C. in a shaking water bath for 30 min, terminated by rapid filtration through Whatman GF/B filters (presoaked in 0.3% polyethyleneimine), and counted in a liquid scintillation counter. Non-specific binding was defined as that remaining in the presence of 3 μM eticlopride. $IC_{50}$ and $K_i$ (Cheng & Prusoff, 1973) calculations were performed using nonlinear regression one-site competition analysis (GraphPad, Prism), with top and bottom limits held constant at 0% and 100% inhibition, respectively. The percent inhibition at each drug concentration was the average of duplicate determinations.

The ligand $K_d$ used in the $K_i$ calculation was determined using both saturation analysis (Scatcharad, 1949) as well as kinetic analysis (association and dissociation rates). (See Creese, I., Burt, et al., Science 192: 481–483 (1978); Dal Toso, et al., EMBO J. 8:4025–4034 (1989); H. Hall, et al., J. Neurochem. 55:2048–2057 (1990); Cheng, Y. et al., Biochem. Pharmacol. 22: 3099–3108 (1973); and Scatchard, G. Ann. NY Acad. Sci. 51: 660–672 (1949).

CLIMBING MOUSE ASSAY (CMA)

This test may be used as to identify compounds useful in treating psychosis. Costall, B. et al, *Eur. J. Pharm.* 50: 39–50 (1978); Protais, P., et al., *Psychopharmacology* 50:1–6 (1976). Apomorphine induces climbing in mice at low dose levels which do not induce oral stereotypy or motor stimulation. This effect of apomorphine is antagonized by the $D_2$ receptor antagonist.

CD-1 male mice (20–30 grams) are assigned to groups of 8 and individually placed in wire mesh stick cages and allowed one hour for adaptation to new environment. Apomorphine is injected at 1.5 mg/kg subcutaneously which is a dose which causes climbing in all subjects for thirty minutes. Test compounds are administered intraperitoneally thirty minutes prior to the apomorphine administration at a dose of 20 mg/kg.

For evaluation of climbing, three readings are taken at ten, twenty and thirty minutes after apomorphine administration according to the following scale:

| Climbing Behavior | Score |
| --- | --- |
| Mice with | |
| 4 paws on bottom (no climbing) | 0 |
| 2 paws on the wall (rearing) | 1 |
| 4 paws on the wall (full climb) | 2 |

The climbing scores are individually totaled (maximal score: 6 per mouse over three readings) and total score of the control (vehicle intraperitoneally (ip) and apomorphine subcutaneous) is set to 100%. $ED_{50}$ values with 95% confidence limits calculated by a linear regression analysis of some of the compounds of the present invention as well as a standard antipsychotic agent (clozapine) are presented in Table 1.

TABLE I

| X AND Y | $R_1$ | $R_2$ | $R_3$ | Clozapine | ED50 (mg/kg/ip) |
| --- | --- | --- | --- | --- | --- |
| OH | $CH_2CH_2Ph$ | H | H | 8.1 | 8.1 |
| $OCH_3$ | $(CH_2)_2$-COPh-4-F | H | C(O)H | 8.1 | 19.6 |
| OH | $CH_2CH_2Ph$ | H | $CH_3$ | 8.1 | 6.9 |
| OH | $(CH_2)_3$-6-F-benzis. | H | H | 8.1 | 16.0 |
| acetyl | $CH_2CH_2Ph$ | H | H | 8.1 | 11.1 |

Ph = phenyl; benzis. = benzisoxazole; F = fluoro; all X & Y. positions at 5, 6 and n = 1.

An [N-methyl-$^3$H]spiroperidol[$^3$H]NMSP test to cloned human dopamine D2Long receptors was used to demonstrate that compounds of the present invention bind at the D2 receptor. [N-methyl$^3$H]spiroperidol was chosen as a ligand for its affinity for the D2 receptor (Hall, H. et al., *J. Neuroschem.* 55:2048–2057 (1990) and Leysen, J. E., et al., *Biochem. Pharmacol.* 27: 307–328 (1977)).

For most assays, a 100 mM stock solution of test compound with solvent and buffer is prepared so that concentrations of $10^{-5}$ to $10^{-8}$M are attained. Cheng-Prisoff determination (Ki's) are performed using Prism software.

TABLE 2

Bindingg to Human D2Long Receptors*

| X and Y | $R_1$ | $R_2$ | $R_3$ | Ki (μm) |
| --- | --- | --- | --- | --- |
| 5,6-OH | $SO_2CH_3$ | H | H | 4.2 |
| 5,6-OH | $CH_2CH_3$ | H | H | 2.51 |
| 5,6-OH | $CH_2CH_2Ph$ | H | H | 1.09 |
| 5,6-OH | $(CH_2)_3$-6-F-benzisoxaole | H | H | 0.178 |
| 5,6-OAc | $CH_2CH_2Ph$ | H | H | 1.52 |
| 5,6-cyclohexyl-idinedioxy | $(CH_2)_3$—OPh, (2-$OCH_3$, 4-$COCH_3$) | H | $CH{=}O$ | 0.857 |
| 5,6-OH | $(CH_2)_3$—OPh, (2-$OCH_3$, 4-$COCH_3$) | H | H | 1.1 |
| 5,6-cyclohexyl-idineioxy | $CH_2CH_2$-thiophen-2-yl | H | $CH{=}O$ | 0.506 |
| 5,6-cyclohexyl-idinedioxy | $CH_2)_3CH$—(Ph-4-F)$_2$ | H | $CH{=}O$ | 0.639 |
| 5,6-OH | $CH_2CH_2Ph(4$-$OCH_3)$ | H | H | 1.2 |
| 5,6-OH | $CH_2CH_2Ph(4$-$Cl)$ | H | H | 0.505 |
| 5,6-OH | $CH_2CH_2Ph(4$-$OCH_3)$ | H | $CH_3$ | 2.5 |
| 5,6-OH | $CH_2CH_2$thiophen-2-yl | H | H | 2.1 |
| 5,6-OH | $(CH_2)_3CH$—(Ph-4-F)$_2$ | H | H | 0.0918 |
| 5,6-OH | $CH_2CH_2Ph(2$-$CH_3)$ | H | H | 0.684 |
| 5,6-OH | $CH_2CH_2O$—Ph | H | H | 0.5 |
| 5,6-OH | H | H | H | 3.9 |
| 5,6-OH | $CH_2CH_2Ph(4$-$Cl)$ | H | $CH_3$ | 0.413 |
| 5,6-OH | $(CH_2)_3$1,3-dihydro-benzimidazol-2-one | H | H | 0.432 |
| 5,6-cyclohexyl-idinedioxy | $(CH_2)_3CH(Ph$-$4$-$F)_2$ | H | H | 0.153 |
| Reference drug: Clozapine | | | | 0.33 |

*All compounds listed are from Formula I where n = 1;
Ph = phenyl; Ac = acetyl; Ph-4 = phenyl para-substituted; Ph-2 = phenyl ortho-substituted.

The compounds of the present invention may be shown to be effective in treating psychosis in human beings by administering the compound to a patient suffering from psychosis and observing the behavior of the patient. These observations may be assessed by standard tests such as the Abbreviated Hamilton Psychiatric Rating Scale where certain scores are given for defined behavior.

Other compounds of Formula I, preferably wherein n=1 and X and Y are preferably 5,6-$C_{1-6}$alkoxy, hydroxy and more preferably methoxy at positions 5 and 6; or X and Y together form cyclohexylideneketal are shown in Table 3.

TABLE 3

| $R_1$ | $R_2$ | $R_3$ |
| --- | --- | --- |
| 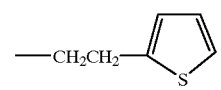 | H | $CH_3$ |

TABLE 3-continued

| $R_1$ | $R_2$ | $R_3$ |
|---|---|---|
| 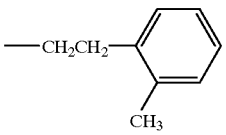 | H | CH₃ |
| 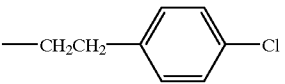 | H | H |
| 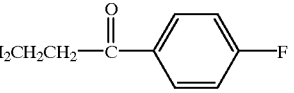 | H | H |
| 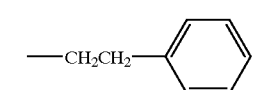 | H | CH₃ |
| 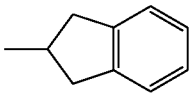 | H | CH₃ |
| 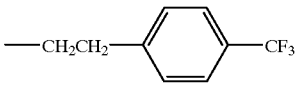 | H | CH₃ |
| 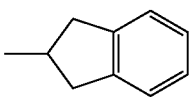 | H | CH₃ |
| 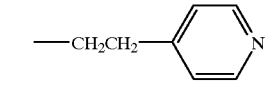 | H | H |
| 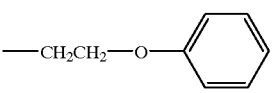 | H | H |
| 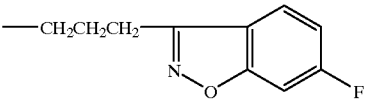 | H | CH₃ |
| 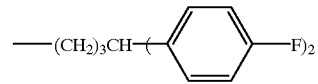 | H | CH₃ |
| 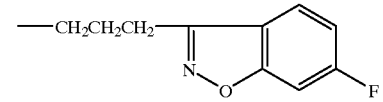 | H | CH₃ |
| 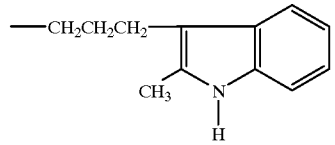 | H | CH₃ |
| 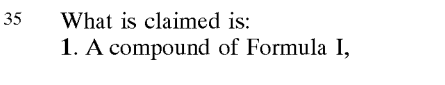 | H | CH₃ |
| 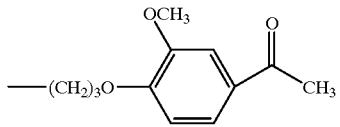 | H | CH₃ |
| 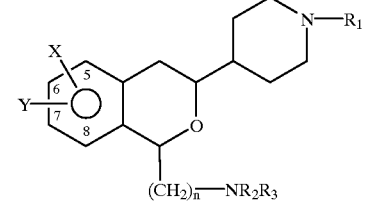 | H | CH₃ |
| 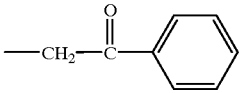 | H | CH₃ |
|  | H | CH₃ |
| 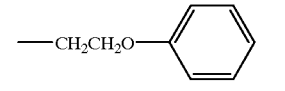 | CH₃ | CH₃ |

What is claimed is:
1. A compound of Formula I,

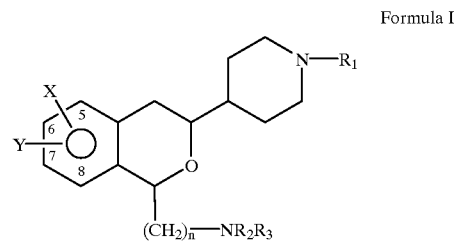

Formula I a stereoisomer, or a pharmaceutically acceptable salt thereof, wherein $R_1$ is H, $C_{1-6}$ alkyl, optionally substituted aralkyl selected from optionally substituted phenyl-$C_{1-6}$ alkyl and optionally substituted diphenyl-$C_{1-6}$ alkyl, optionally substituted heteroarylalkyl selected from thiophene, furan, pyrrol, imidazole, pyrazole, isothiazole, isoxazole, pyran, pyridine, pyrazine, pyrimidine, pyridazine, benzothiophene, chromene, indolizine, isoindole, indole, indazole, quinoline, 2-oxo-2,3-dihydrobenzimidazole, phthalazine, quinazoline, cinnoline, isochroman, chroman, 1,2-benzenedicarboximide and benzisoxazole; 5,5-dimethyl-1,1-dioxo-4-thiazolidinone, indan, alkylsulfonyl, trifluoroacetyl, or $(CH_2)_m Z(CH_2)_r$-optionally substituted phenyl, wherein Z is O or C=O;
wherein optionally substituted means a moiety is suitably substituted with one, two or three substituents each independently selected from H, halogen, $C_{1-6}$ alkyl, $C_{1-6}$ alkoxy, $C(=O)H$, $C(=O)C_{1-6}$ alkyl, $CF_3$ or hydroxy;

each of $R_2$ and $R_3$ are independently H, $C_{1-6}$ alkyl, $C(O)C_{1-6}$ alkyl, CHO, or $C_{2-6}$ alkenyl;

each of X and Y are independently H, hydroxy, $C_{1-6}$ alkyl, halogen, acyloxy or $C_{1-6}$ alkoxy, benzyloxy, or X and Y together form a diphenylmethylene ketal, methylene acetal, cyclohexylideneketal, or cyclic carbonate group provided that X and Y are adjacently positioned; and n is an integer 1, 2 or 3;

m is an integer 0, 1, 2 or 3; and t is an integer 0, 1, 2 or 3.

2. The compound of claim 1 wherein
$R_1$ is $C_{1-6}$alkyl, aralkyl, or heteroaralkyl;
each of $R_2$ and $R_3$ are independently hydrogen, or $C_{1-6}$alkyl; and
each of X and Y are independently hydroxy, acyloxy, or $C_{1-6}$alkyl; and
n is 1.

3. The compound of claim 1 wherein
each of X and Y are hydroxy, $C_{1-6}$alkoxyl or acyloxy;
each of X and Y are respectively at positions 5 and 6; and
n is 1.

4. The compound of claim 1 wherein n is 1.

5. The compound of claim 1 wherein X and Y are each methoxy.

6. The compound of claim 1 wherein each $C_{1-6}$alkyl and each $C_{1-6}$alkoxy respectively are $C_{1-4}$alkyl and $C_{1-4}$alkoxy.

7. The compound of claim 1 wherein X and Y are each hydroxy and respectively at positions 5 and 6.

8. The compound of claim 1 wherein $R_1$ is aralkyl.

9. The compound of claim 1 wherein $R_1$ is optionally substituted heteroaralkyl.

10. The compound of claim 1 wherein $R_1$ is phenylethyl.

11. The compound of claim 1 wherein $R_1$ is (6-fluoro-1,2-benzisoxazol-3-yl)propyl.

12. The compound of claim 1 wherein optionally substituted aralkyl is an optionally substituted benzyl, optionally substituted phenylethyl or optionally substituted phenylpropyl.

13. The compound of claim 1 wherein the heteroaralkyl is an optionally substituted 1,2-benzisoxazolyl.

14. The compound of claim 13 wherein heteroaralkyl is (6-fluoro-1,2-benzisoxazol-3-yl)propyl.

15. The compound of claim 1 wherein one of X and Y are H.

16. The compound of claim 1 wherein the compound is cis-N-[3-(1-acetyl-4-piperidinyl)-3,4-dihydro-5,6-dimethoxy-1H-2-benzopyran-1-ylmethyl]formamide.

17. The compound of claim 1 wherein the compound is cis-N-[3,4-dihydro-5,6-dimethoxy-3-[1-(methylsulfonyl)-4-piperidinyl]-1H-2-benzopyran-1-ylmethyl]formamide.

18. The compound of claim 1 wherein the compound is cis-1-(aminomethyl)-3,4-dihydro-5,6-dimethoxy-3-(1-methylsulfonyl-4-piperidinyl)-1H-2-benzopyran.

19. The compound of claim 1 wherein the compound is cis-N-[3,4-dihydro-5,6-dimethoxy-3-[1-(2-phenylethyl)-4-piperidinyl]-1H-2-benzopyran-1-ylmethyl]formamide.

20. The compound of claim 1 wherein the compound is cis-1-(aminomethyl)-3,4-dihydro-5,6-dimethoxy-3-[1-(2-phenylethyl)-4-piperidinyl]-1H-2-benzopyran.

21. The compound of claim 1 wherein the compound is cis-1-(aminomethyl)-3,4-dihydro-3-[1-(2-phenylethyl)-4-piperidinyl]-1H-2-benzopyran-5,6-diol.

22. The compound of claim 1 wherein the compound is cis-1-(aminomethyl)-5,6-diacetoxy-3,4-dihydro-3-[1-(2-phenylethyl)-4-piperidinyl]-1H-2-benzopyran.

23. The compound of claim 1 wherein the compound is cis-N-[3,4-dihydro-5,6-dimethoxy-3-(1-trifluoroacetyl-4-piperidinyl)-1H-2-benzopyran-1-ylmethyl]formamide.

24. The compound of claim 1 wherein the compound is cis-N-[3,4-dihydro-5,6-dimethoxy-3-(4-piperidinyl)-1H-2-benzopyran-ylmethyl]formamide.

25. The compound of claim 1 wherein the compound is cis-N-[3-[1-[4-(4-fluorophenyl)-4-oxobutyl]-4-piperidinyl]-3,4-dihydro-5,6-dimethoxy-1H-2-benzopyran-1-ylmethyl]formamide.

26. The compound of claim 1 wherein the compound is cis-1-(aminomethyl)-3,4-dihydro-3-(1-ethyl-4-piperidinyl)-1H-2-benzopyran-5,6-diol.

27. The compound of claim 1 wherein the compound is cis-1-(aminomethyl)-3,4-dihydro-3-[1-[3-(6-fluoro-1,2-benzisoxazol-3-yl]propyl]-4-piperidinyl]-1H-2-benzopyran-5,6-diol.

28. The compound of claim 1 wherein the compound is cis-1-(aminomethyl)-3,4-dihydro-3-[1-(3-phenylpropyl)-4-piperidinyl]-1H-2-benzopyran-5,6-diol.

29. The compound of claim 1 wherein the compound is cis-1-(aminomethyl)-3,4-dihydro-5,6-dimethoxy-3-(1-benzyl-4-piperidinyl)-1H-2-benzopyran.

30. The compound of claim 1 wherein the compound is cis-1-(aminomethyl)-3-(1-benzyl-4-piperidinyl)-3,4-dihydro-1H-2-benzopyran-5,6-diol.

31. The compound of claim 1 wherein the compound is cis-1-(N-methylaminomethyl)-3,4-dihydro-3-[1-(2-phenylethyl)-4-piperidinyl]-1H-2-benzopyran-5,6-diol.

32. The compound of claim 1 wherein the compound is cis-1-aminomethyl-3,4-dihydro-3-[1-(methylsulfonyl)-4-piperidinyl]-1H-2-benzopyran-5,6-diol.

33. The compound of claim 1 wherein the compound is 1-[4-[cis-1-((aminomethyl)-3,4-dihydro-5,6-dimethoxy-1H-2-benzopyran-3-yl]piperidin-1-yl]-2-(4-fluorophenyl)ethanone.

34. The compound of claim 1 wherein the compound is cis-1-(aminomethyl)-3,4-dihydro-3-[1-[2-(4-fluorophenethyl)]-4-piperidinyl]-1H-2-benzopyran-5,6-diol.

35. The compound of claim 1 wherein the compound cis-3,4-dihydro-5,6-dimethoxy-2-[1-[2-(4-fluorophenethyl)]-4-piperidinyl]-1-(N-methylaminomethyl)-1H-2-benzopyran.

36. The compound of claim 1 wherein the compound is cis-1-3,4-dihydro-3-[1-[2-(4-fluorophenylethyl)]-4-piperidinyl]-(N-methylaminomethyl)-1H-2-benzopyran-5,6-diol.

37. The compound of claim 1 wherein the compound is cis-N-[3,4-dihydro-5,6-dimethoxy-3-[1-(2-phenethyl)-4-piperidinyl]-1H-2-benzopyran-1-yl]formamide.

38. The compound of claim 1 wherein the compound is cis-1-(aminomethyl)-3,4-dihydro-3-[1-(2-phenylethyl)-4-piperidinyl]-1H-2-benzopyran-5,6-diol.

39. The compound of claim 1 wherein the compound is cis-1-(aminomethyl)-3,4-dihydro-3-4-(piperidinyl)-1H-2-benzopyran-5,6-diol.

40. The compound of claim 1 wherein the compound is cis-3,4-dihydro-3-[4-[2-(4-methoxyphenyl)ethyl]-4-piperidinyl]-1(N-methylaminomethyl)-1H-2-benzopyran-5,6-diol.

41. The compound of claim 1 wherein the compound is cis-1-(aminomethyl)-3,4-dihydro-3-[1-[2-(4-methoxyphenyl)-ethyl]-4-piperidinyl]-1H-2-benzopyran-5,6-diol.

42. The compound of claim 1 wherein the compound is cis-1-(aminomethyl)-3-[1-[2-(4-chlorophenyl)ethyl]-3,4-dihydro-4-piperidinyl]-1H-2-benzopyran-5,6-diol.

43. The compound of claim 1 wherein the compound is cis-3-[1-[2-(4-chlorophenyl)ethyl]-3,4-dihydro-4-piperidinyl]-1-(N-methylaminomethyl)-1H-2-benzopyran-5,6-diol.

44. The compound of claim 1 wherein the compound is cis-3,4-dihydro-5,6-dimethoxy-3-[1-[2-(4-fluorophenylethyl)]-4-piperidinyl]-1-(N-methylaminomethyl)-1H-2-benzopyran.

45. The compound of claim 1 wherein the compound is cis-3,4-dihydro-3-[1-[2-(4-fluorophenethyl)]-4-piperidinyl](N-methylaminomethyl)-1H-2-benzopyran-5,6-diol.

46. The compound of claim 1 wherein the compound is cis-1-(aminomethyl)-5,6-diacetoxy-3,4-dihydro-3-[1-(2-phenethyl)-4-piperidinyl]-1H-2-benzopyran.

47. The compound of claim 1 wherein the compound is cis-3,4-dihydro-3-[1-[2-(4-fluorophenylethyl)]-4-piperidinyl]-(N-methylaminomethyl)-1H-2-benzopyran-5,6-diol.

48. The compound of claim 1 wherein the compound is cis-N-[3,4-dihydro-5,6-dimethoxy-3-[1-(2-phenylethyl)-4-piperidinyl]-1H-2-benzopyran-1-ylmethyl]formamide.

49. The compound of claim 1 wherein the compound is cis-1-(aminomethyl)-3,4-dihydro-3-[1-(2-phenethyl)-4-piperidinyl]-1H-2-benzopyran-5,6-diol.

50. The compound of claim 1 wherein the compound is cis-N-[3-[1-[4-(4-fluorophenyl)-4-oxobutyl]piperidinyl-4-yl]-3,4-dihydro-5,6-dimethoxy-1H-2-benzopyran-1-ylmethyl]formamide.

51. The compound of claim 1 wherein the compound is cis-N-[5,6-(cyclohexylidenedioxy)-3,4-dihydro-3-(4-piperidinyl)-1H-2-benzopyran-1-ylmethyl]formamide.

52. The compound of claim 1 wherein the compound is cis-1-(aminomethyl)3,4-dihydro-3-[1-(2-phenoxyethyl)-4-piperidinyl]-1H-2-benzopyran-5,6-diol.

53. The compound of claim 1 wherein the compound is cis-N-[5,6-(cyclohexylidenedioxy)-3,4-dihydro-3-[1-(2-(thiophen-2-yl)ethyl)piperidin-4-yl]1H-2-benzopyran-1-yl]formamide.

54. The compound of claim 1 wherein the compound is cis-1-(aminomethyl)-3,4-dihydro-2-[1-(3-thiophen-2-ylethyl)-4-piperidinyl]-1H-2-benzopyran-5,6-diol.

55. The compound of claim 1 wherein the compound is cis-1-(aminomethyl)-3,4-dihydro-3-[1-[2-(2-methylphenyl)propyl]-4-piperidinyl]-1H-2-benzopyran-5,6-diol.

56. The compound of claim 1 wherein the compound is cis-N[5,6-(cyclohexylidenedioxy)-3,4-dihydro-3-(1-trifluoroacetyl-4-piperidinyl)-1H-2-benzopyran-1-ylmethyl]formamide.

57. The compound of claim 1 wherein the compound is cis-N-[3-[1-[4,4-bis-(4-fluorophenyl)butyl]-4-piperidinyl]-5,6-(cyclohexylidenedioxy)-3,4-dihydro-1H-2-benzopyran-1-ylmethyl]formamide.

58. The compound of claim 1 wherein the compound is cis-1-(aminomethyl)-3-[1-[4,4-bis-(4-fluorophenyl)butyl]-4-piperidinyl]-3,4-dihydro-1H-2-benzopyran-5,6-diol.

59. The compound of claim 1 wherein the compound is cis-N-[3-[1-[3-(4-acetyl-2-methoxyphenoxy)propyl]-4-piperidinyl]-5,6-(cyclohexylidenedioxy)-3,4-dihydro-1H-2-benzopyran-1-ylmethyl]formamide.

60. The compound of claim 1 wherein the compound is cis-1-[3-[3-[4-[1-(aminomethyl)-3,4-dihydro-5,6-dihydroxy-1H-2-benzopyran-3-yl]-1-piperidinyl]propoxy]-3-methoxyphenyl]ethanone.

61. The compound of claim 1 wherein the compound is cis-N-[3-(1-Acetyl-4-piperidinyl)-3,4-dihydro-5,6-dimethoxy-1-1H-2-benzopyran-1-ylmethyl]formamide.

62. The compound of claim 1 wherein the compound is cis-1-(Aminomethyl)-3,4-dihydro-3-(4-piperidinyl)-1H-2-benzopyran-5,6-diol.

63. The compound of claim 1 wherein the compound is cis-1-[3-[4-(1-Aminomethyl-3,4-dihydro-5,6-dihydroxy-1H-2-benzopyran-3-yl)-1-piperidinyl]propyl]-1,3-dihydrobenzimidazol-2-one.

64. The compound of claim 1 wherein the compound is cis-1-[3-[4-(1-Aminomethyl-3,4-dihydro-5,6-dihydroxy-1H-2-benzopyran-3-yl)-1-piperidinyl]propyl]-1,3-dihydrobenzimidazol-2-one.

65. The compound of claim 1 wherein the compound is cis-N-[5,6-(Cyclohexylidenedioxy)-3,4-dihydro-3-[1-[3-(2-oxo-2,3-dihydrobenzimidazole-1-yl)propyl]-4-piperidinyl]-1H-2-benzopyran-1-ylmethyl)]formamide.

66. The compound of claim 1 wherein the compound is cis-1-(Aminomethyl)-3,4-dihydro-3-[1-[2-(3-chlorophenyl)]-4-piperidinyl]-1H-2-benzopyran-5,6-diol.

67. The compound of claim 1 wherein the compound is cis-N-[5,6-(Cyclohexylidenedioxy)-3,4-dihydro-3-[1-[2-(4-methoxyphenyl)ethyl]-4-piperidinyl]-1H-2-benzopyran-1-ylmethyl]formamide.

68. The compound of claim 1 wherein the compound is cis-1-Aminomethyl-5,6-(cyclohexylidenedioxy)-3,4-dihydro-3-[1-[4,4-bis(4-fluorophenyl)butyl]-4-piperidinyl]-1H-2-benzopyran.

69. The compound of claim 1 wherein the compound is cis-1-(Aminomethyl)-3,4-dihydro-3-[1-[3-(2-methyl-1H-indol-3-yl)propyl]-4-piperidinyl]-1H-2-benzopyran-5,6-diol.

70. The compound of claim 1 wherein the compound is cis-1-(Aminomethyl)-3,4-dihydro-3-[1-[2-(4-trifluoromethylphenyl)ethyl]-4-piperidinyl]-1H-2-benzopyran-5,6-diol.

71. The compound of claim 1 wherein the compound is cis-N-[3-[1-[2-(4-Chlorophenyl)ethyl]-4-piperidinyl]-5,6-(cyclohexylidenedioxy)-3,4-dihydro-1H-2-benzopyran-1-ylmethyl]formamide.

72. A pharmaceutical composition comprising a therapeutically effective amount of the compound of claim 1 and a pharmaceutically acceptable carrier.

73. A method of treating a patient for a psychotic disorder by administering to the patient an antipsychotic therapeutically effective amount of the command of claim 1.

74. The method of claim 73 wherein the psychotic disorder is schizophrenia.

75. A method of making a compound of formula I:

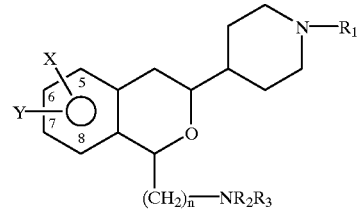

Formula I a stereoisomer, or a pharmaceutically acceptable salt thereof, wherein $R_1$ is H, $C_{1-6}$ alkyl, optionally substituted aralkyl selected from optionally substituted phenyl-$C_{1-6}$alkyl and optionally substituted diphenyl-$C_{1-6}$alkyl, optionally substituted heteroarylalkyl selected from thiophene, furan, pyrrol, imidazole, pyrazole, isothiazole, isoxazole, pyran, pyridine, pyrazine, pyrimidine, pyridazine, benzothiophene, chromene, indolizine, isoindole, indole, indazole, quinoline, 2-oxo-2,3-dihydrobenzimidazole, phthalazine, quinazoline, cinnoline, isochroman, chroman, 1,2-benzenedicarboximide and benzisoxazole; 5,5 methyl-1,1-dioxo-4-thiazolidinone, indan, alkylsulfonyl, trifluoroacetyl, or $(CH_2)_m Z(CH_2)_t$-optionally substituted phenyl, wherein Z is O or C=O;

wherein optionally substituted means a moiety is suitably substituted with one, two or three substituents each independently selected from H, halogen, $C_{1-6}$ alkyl, $C_{1-6}$ alkoxy, C(=O)H, C(=O)$C_{1-6}$ alkyl, $CF_3$ or hydroxy;

each of $R_2$ and $R_3$ are independently H, $C_{1-6}$ alkyl, C(O)$C_{1-6}$ alkyl, CHO, or $C_{2-6}$ alkenyl;

each of X and Y are independently H, hydroxy, $C_{1-6}$ alkyl, halogen, acyloxy or $C_{1-6}$ alkoxy, benzyloxy, or X and Y together form a diphenylmethylene ketal, methylene acetal, cyclohexylideneketal, or cyclic carbonate group provided that X and Y are adjacently positioned; and n is an integer 1, 2 or 3;

m is an integer 0, 1, 2 or 3; and t is an integer 0, 1, 2 or 3;

comprising the steps of:

a) deprotecting compound 17 wherein X' and Y' each respectively are X and Y except for hydroxy and Pg is a suitable protecting group

17

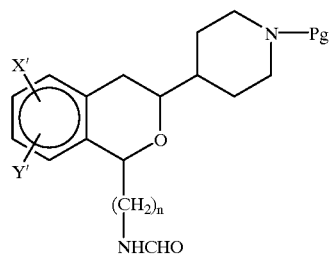

to produce compound 18;

18

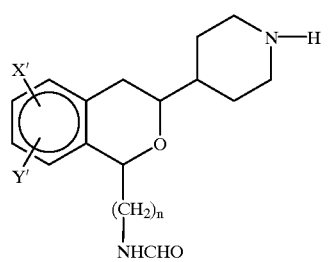

b) optionally reacting compound 18 with $R_1$'-Lg, wherein Lg is a suitable leaving group and $R_1$' is $R_1$ except for hydrogen, to produce compound 19;

19

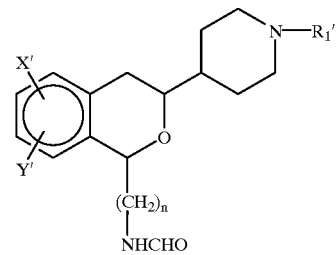

c) optionally mono or dialkylating the amine wherein $R_2$' is hydrogen and $R_3$' is hydrogen or $C_{1-6}$alkyl, to produce compound 20;

20

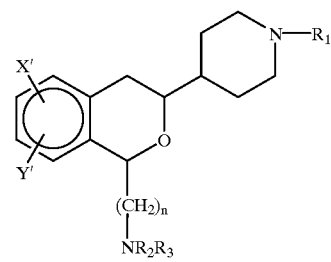

d) optionally deprotecting compounds 18, 19 or 20, when one of X' or Y' is $C_{1-6}$alkoxy or benzyloxy or when X' and Y' form a diphenylmethylene ketal, methylene acetal, cyclohexylidene ketal or cyclic carbonate group, to produce compound 21 wherein one of X" or Y" are hydroxy and $R_2$" and $R_3$" are each hydrogen, formyl or $C_{1-6}$alkyl;

21

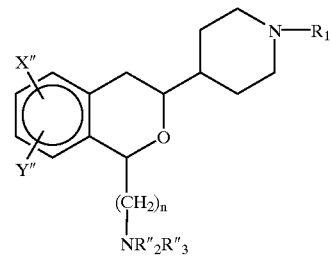

e) optionally acylating compound 21 when at least one of X" or Y" is hydroxy to produce compound 22 wherein at least one of Xa and Ya is acyloxy.

22

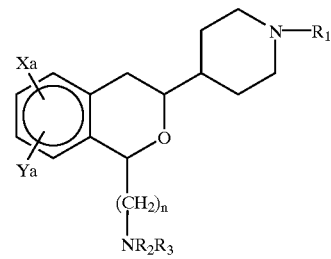

* * * * *